(12) United States Patent
Nelson et al.

(10) Patent No.: US 7,914,533 B2
(45) Date of Patent: Mar. 29, 2011

(54) MINIMALLY INVASIVE ACTUABLE BONE FIXATION DEVICES

(75) Inventors: Charles L. Nelson, Santa Rosa, CA (US); Heber Saravia, Santa Rosa, CA (US); Kai U. Mazur, Santa Rosa, CA (US)

(73) Assignee: Sonoma Orthopedic Products, Inc., Santa Rosa, CA (US)

( * ) Notice: Subject to any disclaimer, the term of this patent is extended or adjusted under 35 U.S.C. 154(b) by 1119 days.

(21) Appl. No.: 11/565,534

(22) Filed: Nov. 30, 2006

(65) Prior Publication Data
US 2007/0233105 A1 Oct. 4, 2007

Related U.S. Application Data

(63) Continuation of application No. 11/383,269, filed on May 15, 2006.

(60) Provisional application No. 60/682,652, filed on May 18, 2005.

(51) Int. Cl.
*A61B 17/56* (2006.01)
(52) U.S. Cl. ............................................ 606/64; 606/62
(58) Field of Classification Search .............. 606/62–68, 606/86 R, 300–331
See application file for complete search history.

(56) References Cited

U.S. PATENT DOCUMENTS

| | | | |
|---|---|---|---|
| 958,127 A | 5/1910 | Hufrud | |
| 1,169,635 A | 1/1916 | Grimes | |
| 1,790,841 A | 2/1931 | Rosen | |
| 2,502,267 A | 3/1950 | McPherson | |
| 2,685,877 A | 8/1954 | Dobelle | |
| 2,998,007 A | 8/1961 | Herzog | |
| 3,118,444 A | 1/1964 | Serrato, Jr. | |
| 3,626,935 A | 12/1971 | Pollock et al. | |
| 3,710,789 A | 1/1973 | Ersek | |
| 3,759,257 A | 9/1973 | Fischer et al. | |
| 3,760,802 A * | 9/1973 | Fischer et al. | ............... 606/63 |
| 3,779,239 A * | 12/1973 | Fischer et al. | ............... 606/63 |

(Continued)

FOREIGN PATENT DOCUMENTS

CA 2561552 A1 11/2005

(Continued)

OTHER PUBLICATIONS

Nelson, Charles; U.S. Appl. No. 11/383,800 entitled "Deployable intramedullary stent system for reinforcement of bone," filed May 17, 2006.

(Continued)

*Primary Examiner* — Eduardo C Robert
*Assistant Examiner* — Jan Christopher Merene
(74) *Attorney, Agent, or Firm* — Kilpatrick Townsend Stockton LLP

(57) ABSTRACT

Apparatus for bone reinforcement, fixation and treatment of diseased or fractured bones including a supporting structure optionally coated with therapeutic agent is provided. The supporting structure or device may be collapsible upon deployment at the surgical site, and include fixation features such as anchors to securely position in place once deployed. Bone cement or other material may be provided to alternatively secure the positioned supporting structure for treatment. A lockable bone fixation device is described that comprises: a sleeve adapted to be positioned in a space formed in a bone; a guidewire adapted to guide movement of the sleeve; and an actuable lock adapted to secure the sleeve within the space of the bone from an end of the device.

10 Claims, 23 Drawing Sheets

U.S. PATENT DOCUMENTS

| | | |
|---|---|---|
| 3,791,380 A | 2/1974 | Dawidowski |
| 3,846,846 A * | 11/1974 | Fischer ..................... 623/23.18 |
| 3,955,565 A | 5/1976 | Johnson, Jr. |
| 3,978,528 A | 9/1976 | Crep |
| 3,986,504 A | 10/1976 | Avila |
| 4,007,528 A | 2/1977 | Shea et al. |
| 4,011,602 A | 3/1977 | Rybicki et al. |
| 4,016,874 A | 4/1977 | Maffei et al. |
| 4,091,806 A | 5/1978 | Aginsky |
| 4,146,022 A | 3/1979 | Johnson et al. |
| 4,164,794 A | 8/1979 | Spector et al. |
| 4,190,044 A | 2/1980 | Wood |
| D255,048 S | 5/1980 | Miller |
| 4,204,531 A | 5/1980 | Aginsky |
| 4,227,518 A | 10/1980 | Aginsky |
| 4,236,512 A | 12/1980 | Aginsky |
| 4,237,875 A | 12/1980 | Termanini |
| 4,246,662 A | 1/1981 | Pastrick |
| 4,262,665 A | 4/1981 | Roalstad et al. |
| 4,275,717 A | 6/1981 | Bolesky |
| 4,293,962 A | 10/1981 | Fuson |
| 4,294,251 A | 10/1981 | Greenwald et al. |
| 4,312,336 A | 1/1982 | Danieletto et al. |
| 4,338,926 A | 7/1982 | Kummer et al. |
| 4,351,069 A | 9/1982 | Ballintyn et al. |
| 4,352,212 A | 10/1982 | Greene et al. |
| 4,379,451 A | 4/1983 | Getscher |
| 4,409,974 A | 10/1983 | Freedland |
| 4,453,539 A | 6/1984 | Raftopoulos et al. |
| 4,457,301 A | 7/1984 | Walker |
| 4,462,394 A | 7/1984 | Jacobs |
| 4,467,794 A | 8/1984 | Maffei et al. |
| RE31,809 E | 1/1985 | Danieletto et al. |
| 4,492,226 A | 1/1985 | Belykh et al. |
| 4,503,847 A | 3/1985 | Mouradian |
| 4,519,100 A | 5/1985 | Wills et al. |
| 4,520,511 A | 6/1985 | Gianezio et al. |
| 4,522,200 A | 6/1985 | Stednitz |
| 4,552,136 A | 11/1985 | Kenna |
| 4,589,883 A | 5/1986 | Kenna |
| 4,590,930 A | 5/1986 | Kurth et al. |
| 4,604,997 A | 8/1986 | De Bastiani et al. |
| 4,621,627 A | 11/1986 | De Bastiani et al. |
| 4,622,959 A | 11/1986 | Marcus |
| 4,628,920 A | 12/1986 | Mathys, Jr. et al. |
| 4,632,101 A | 12/1986 | Freedland |
| 4,643,177 A | 2/1987 | Sheppard et al. |
| 4,651,724 A | 3/1987 | Berentey et al. |
| 4,653,487 A | 3/1987 | Maale |
| 4,667,663 A | 5/1987 | Miyata |
| D290,399 S | 6/1987 | Kitchens |
| 4,681,590 A | 7/1987 | Tansey |
| 4,697,585 A | 10/1987 | Williams |
| 4,705,027 A | 11/1987 | Klaue |
| 4,705,032 A | 11/1987 | Keller |
| 4,721,103 A | 1/1988 | Freedland |
| 4,776,330 A | 10/1988 | Chapman et al. |
| 4,781,181 A | 11/1988 | Tanguy |
| 4,805,607 A | 2/1989 | Engelhardt et al. |
| 4,813,963 A | 3/1989 | Hori et al. |
| 4,817,591 A | 4/1989 | Klaue et al. |
| 4,827,919 A | 5/1989 | Barbarito et al. |
| 4,828,277 A | 5/1989 | De Bastiani et al. |
| 4,854,312 A | 8/1989 | Raftopoulos et al. |
| 4,858,602 A | 8/1989 | Seidel et al. |
| 4,862,883 A | 9/1989 | Freeland |
| 4,871,369 A | 10/1989 | Muller |
| 4,875,475 A | 10/1989 | Comte et al. |
| 4,896,662 A | 1/1990 | Noble |
| 4,921,499 A | 5/1990 | Hoffman et al. |
| 4,927,424 A | 5/1990 | McConnell et al. |
| 4,932,969 A | 6/1990 | Frey et al. |
| 4,943,291 A | 7/1990 | Tanguy |
| 4,946,179 A | 8/1990 | De Bastiani et al. |
| 4,959,066 A | 9/1990 | Dunn et al. |
| 4,969,889 A | 11/1990 | Greig |
| 4,976,258 A | 12/1990 | Richter et al. |
| 4,978,349 A | 12/1990 | Frigg |
| 4,978,358 A | 12/1990 | Bobyn |
| 4,988,349 A | 1/1991 | Pennig |
| 5,002,547 A | 3/1991 | Poggie et al. |
| 5,002,580 A | 3/1991 | Noble et al. |
| 5,006,120 A | 4/1991 | Carter et al. |
| 5,013,314 A | 5/1991 | Firica et al. |
| 5,019,077 A | 5/1991 | De Bastiani et al. |
| 5,026,374 A | 6/1991 | Dezza et al. |
| 5,027,799 A | 7/1991 | Laico et al. |
| 5,030,222 A | 7/1991 | Calandruccio et al. |
| 5,034,012 A | 7/1991 | Frigg |
| 5,034,013 A | 7/1991 | Kyle et al. |
| 5,035,697 A | 7/1991 | Frigg |
| 5,037,423 A | 8/1991 | Kenna |
| 5,041,114 A | 8/1991 | Chapman et al. |
| 5,041,115 A | 8/1991 | Frigg et al. |
| 5,053,035 A | 10/1991 | McLaren |
| 5,057,103 A | 10/1991 | Davis |
| 5,062,854 A | 11/1991 | Noble et al. |
| 5,066,296 A | 11/1991 | Chapman et al. |
| 5,084,050 A | 1/1992 | Draenert |
| 5,092,892 A | 3/1992 | Ashby |
| 5,098,433 A | 3/1992 | Freedland |
| 5,102,413 A | 4/1992 | Poddar |
| 5,108,404 A | 4/1992 | Scholten et al. |
| 5,112,333 A | 5/1992 | Fixel |
| 5,116,335 A | 5/1992 | Hannon et al. |
| 5,116,380 A | 5/1992 | Hewka et al. |
| 5,122,141 A | 6/1992 | Simpson et al. |
| 5,122,146 A | 6/1992 | Chapman et al. |
| 5,124,106 A | 6/1992 | Morr et al. |
| 5,147,408 A | 9/1992 | Noble et al. |
| 5,152,766 A | 10/1992 | Kirkley |
| 5,163,963 A | 11/1992 | Hewka et al. |
| 5,171,324 A | 12/1992 | Campana et al. |
| 5,176,681 A | 1/1993 | Lawes et al. |
| 5,178,621 A | 1/1993 | Cook et al. |
| 5,190,544 A | 3/1993 | Chapman et al. |
| 5,190,546 A | 3/1993 | Jervis |
| 5,192,281 A | 3/1993 | de la Caffiniere |
| 5,197,966 A | 3/1993 | Sommerkamp |
| 5,197,990 A | 3/1993 | Lawes et al. |
| 5,201,735 A | 4/1993 | Chapman et al. |
| 5,201,767 A | 4/1993 | Caldarise et al. |
| 5,263,955 A | 11/1993 | Baumgart et al. |
| 5,268,000 A | 12/1993 | Ottieri et al. |
| 5,281,224 A | 1/1994 | Faccioli et al. |
| 5,292,322 A | 3/1994 | Faccioli et al. |
| 5,295,991 A | 3/1994 | Frigg |
| 5,303,718 A | 4/1994 | Krajicek |
| 5,314,489 A | 5/1994 | Hoffman et al. |
| 5,320,622 A | 6/1994 | Faccioli et al. |
| 5,320,623 A | 6/1994 | Pennig |
| 5,326,376 A | 7/1994 | Warner et al. |
| 5,334,184 A | 8/1994 | Bimman |
| 5,342,360 A | 8/1994 | Faccioli et al. |
| 5,342,362 A | 8/1994 | Kenyon et al. |
| 5,346,496 A | 9/1994 | Pennig |
| 5,350,379 A | 9/1994 | Spievack |
| 5,352,227 A | 10/1994 | O'Hara |
| 5,358,534 A | 10/1994 | Dudasik et al. |
| 5,364,398 A | 11/1994 | Chapman et al. |
| 5,368,594 A | 11/1994 | Martin et al. |
| 5,376,090 A | 12/1994 | Pennig |
| 5,380,328 A | 1/1995 | Morgan |
| 5,383,932 A | 1/1995 | Wilson et al. |
| 5,387,243 A | 2/1995 | Devanathan |
| 5,397,328 A | 3/1995 | Behrens et al. |
| 5,403,321 A | 4/1995 | DiMarco |
| 5,411,503 A | 5/1995 | Hollstien et al. |
| 5,415,660 A | 5/1995 | Campbell et al. |
| 5,417,695 A | 5/1995 | Axelson, Jr. |
| RE34,985 E | 6/1995 | Pennig |
| 5,433,718 A | 7/1995 | Brinker |
| 5,433,720 A | 7/1995 | Faccioli et al. |
| 5,441,500 A | 8/1995 | Seidel et al. |
| 5,443,477 A | 8/1995 | Marin et al. |
| 5,445,642 A | 8/1995 | McNulty et al. |
| 5,454,813 A | 10/1995 | Lawes |

| | | | | | |
|---|---|---|---|---|---|
| 5,454,816 A | 10/1995 | Ashby | 5,779,705 A | 7/1998 | Matthews |
| 5,458,599 A | 10/1995 | Adobbati | 5,782,921 A | 7/1998 | Colleran et al. |
| 5,458,651 A | 10/1995 | Lawes | 5,785,057 A | 7/1998 | Fischer |
| 5,472,444 A | 12/1995 | Huebner et al. | 5,810,750 A | 9/1998 | Buser |
| 5,478,341 A | 12/1995 | Cook et al. | 5,810,820 A | 9/1998 | Santori et al. |
| 5,480,400 A | 1/1996 | Berger | 5,810,830 A | 9/1998 | Noble et al. |
| 5,484,438 A | 1/1996 | Pennig | 5,814,047 A | 9/1998 | Emilio et al. |
| 5,484,446 A | 1/1996 | Burke et al. | 5,814,681 A | 9/1998 | Hino et al. |
| 5,505,734 A | 4/1996 | Caniggia et al. | 5,816,812 A | 10/1998 | Kownacki et al. |
| 5,514,137 A | 5/1996 | Coutts | 5,827,282 A | 10/1998 | Pennig |
| 5,516,335 A | 5/1996 | Kummer et al. | 5,829,081 A | 11/1998 | Pearce |
| 5,520,695 A | 5/1996 | Luckman | 5,836,949 A | 11/1998 | Campbell, Jr. et al. |
| 5,531,748 A | 7/1996 | de la Caffiniere | 5,849,004 A | 12/1998 | Bramlet |
| 5,534,004 A | 7/1996 | Santangelo | 5,849,014 A | 12/1998 | Mastrorio et al. |
| 5,545,162 A | 8/1996 | Huebner | 5,849,035 A | 12/1998 | Pathak et al. |
| 5,549,610 A | 8/1996 | Russell et al. | 5,855,581 A | 1/1999 | Koblish et al. |
| 5,549,706 A | 8/1996 | McCarthy | 5,863,295 A | 1/1999 | Averill et al. |
| 5,554,192 A | 9/1996 | Crowninshield | 5,879,352 A | 3/1999 | Filoso et al. |
| 5,556,433 A | 9/1996 | Gabriel et al. | 5,881,878 A | 3/1999 | Faccioli et al. |
| 5,562,673 A | 10/1996 | Koblish et al. | 5,882,351 A | 3/1999 | Fox |
| 5,562,674 A | 10/1996 | Stalcup et al. | 5,893,850 A | 4/1999 | Cachia |
| 5,562,675 A | 10/1996 | McNulty et al. | 5,895,390 A | 4/1999 | Moran et al. |
| 5,571,189 A | 11/1996 | Kuslich | 5,897,560 A | 4/1999 | Johnson |
| 5,571,204 A | 11/1996 | Nies | 5,902,302 A | 5/1999 | Berki et al. |
| 5,573,536 A | 11/1996 | Grosse et al. | 5,908,422 A | 6/1999 | Bresina |
| 5,578,035 A | 11/1996 | Lin | 5,908,423 A | 6/1999 | Kashuba et al. |
| 5,586,985 A | 12/1996 | Putnam et al. | 5,912,410 A | 6/1999 | Cordell |
| 5,591,169 A | 1/1997 | Benoist | 5,913,867 A | 6/1999 | Dion |
| 5,591,196 A | 1/1997 | Marin et al. | 5,919,194 A | 7/1999 | Anderson |
| 5,593,451 A | 1/1997 | Averill et al. | 5,925,048 A | 7/1999 | Ahmad et al. |
| 5,593,452 A | 1/1997 | Higham et al. | 5,928,235 A | 7/1999 | Friedl |
| 5,605,713 A | 2/1997 | Boltong | 5,928,240 A | 7/1999 | Johnson |
| 5,607,431 A | 3/1997 | Dudasik et al. | 5,931,830 A | 8/1999 | Jacobsen et al. |
| 5,613,970 A | 3/1997 | Houston et al. | 5,931,839 A | 8/1999 | Medoff |
| 5,618,286 A | 4/1997 | Brinker | 5,948,000 A | 9/1999 | Larsen et al. |
| 5,618,300 A | 4/1997 | Marin et al. | 5,948,001 A | 9/1999 | Larsen |
| 5,620,449 A | 4/1997 | Faccioli et al. | 5,951,556 A | 9/1999 | Faccioli et al. |
| 5,624,440 A | 4/1997 | Huebner et al. | 5,951,557 A | 9/1999 | Luter |
| 5,643,258 A | 7/1997 | Robioneck et al. | 5,954,722 A | 9/1999 | Bono |
| 5,645,545 A | 7/1997 | Bryant | 5,954,728 A | 9/1999 | Heller et al. |
| 5,645,599 A | 7/1997 | Samani | 5,964,770 A | 10/1999 | Flomenblit et al. |
| 5,658,283 A | 8/1997 | Huebner | 5,968,047 A | 10/1999 | Reed |
| 5,658,287 A | 8/1997 | Hofmann et al. | 5,976,134 A | 11/1999 | Huebner |
| 5,658,292 A | 8/1997 | Axelson, Jr. | 5,976,147 A | 11/1999 | LaSalle et al. |
| 5,658,293 A | 8/1997 | Vanlaningham | 5,976,188 A | 11/1999 | Dextradeur et al. |
| 5,658,351 A | 8/1997 | Dudasik et al. | 5,989,260 A | 11/1999 | Yao |
| 5,662,648 A | 9/1997 | Faccioli et al. | 5,989,261 A | 11/1999 | Walker et al. |
| 5,662,649 A | 9/1997 | Huebner | 5,993,459 A | 11/1999 | Larsen et al. |
| 5,662,712 A | 9/1997 | Pathak et al. | 6,004,348 A | 12/1999 | Banas et al. |
| 5,665,090 A | 9/1997 | Rockwood et al. | 6,010,505 A | 1/2000 | Asche et al. |
| 5,665,091 A | 9/1997 | Noble et al. | 6,010,506 A | 1/2000 | Gosney et al. |
| 5,681,316 A | 10/1997 | DeOrio et al. | 6,013,081 A | 1/2000 | Burkinshaw et al. |
| 5,681,318 A | 10/1997 | Pennig et al. | 6,015,413 A | 1/2000 | Faccioli et al. |
| 5,683,389 A | 11/1997 | Orsak | 6,017,350 A | 1/2000 | Long |
| 5,683,460 A | 11/1997 | Persoons | 6,019,761 A | 2/2000 | Gustilo |
| 5,688,271 A | 11/1997 | Faccioli et al. | 6,019,762 A | 2/2000 | Cole |
| 5,688,279 A | 11/1997 | McNulty et al. | 6,024,745 A | 2/2000 | Faccioli et al. |
| 5,690,634 A | 11/1997 | Muller et al. | 6,027,506 A | 2/2000 | Faccioli et al. |
| 5,693,047 A | 12/1997 | Meyers et al. | 6,027,534 A | 2/2000 | Wack et al. |
| 5,693,048 A | 12/1997 | Stalcup et al. | 6,033,407 A | 3/2000 | Behrens |
| 5,695,729 A | 12/1997 | Chow et al. | 6,039,742 A | 3/2000 | Krettek et al. |
| 5,697,930 A | 12/1997 | Itoman et al. | 6,045,556 A | 4/2000 | Cohen |
| 5,702,481 A | 12/1997 | Lin | 6,053,922 A | 4/2000 | Krause et al. |
| 5,702,487 A | 12/1997 | Averill et al. | 6,056,756 A | 5/2000 | Eng et al. |
| 5,707,370 A | 1/1998 | Berki et al. | 6,077,264 A | 6/2000 | Chemello |
| 5,718,704 A | 2/1998 | Medoff | 6,080,159 A | 6/2000 | Vichard |
| 5,728,096 A | 3/1998 | Faccioli et al. | 6,093,209 A | 7/2000 | Sanders |
| 5,741,256 A | 4/1998 | Bresina | 6,096,040 A | 8/2000 | Esser |
| 5,741,266 A | 4/1998 | Moran et al. | 6,102,911 A | 8/2000 | Faccioli et al. |
| 5,749,872 A | 5/1998 | Kyle et al. | 6,106,528 A | 8/2000 | Durham et al. |
| 5,749,880 A | 5/1998 | Banas et al. | 6,120,504 A | 9/2000 | Brumback et al. |
| 5,759,184 A | 6/1998 | Santangelo | 6,120,509 A | 9/2000 | Wheeler |
| 5,766,178 A | 6/1998 | Michielli et al. | 6,126,661 A | 10/2000 | Faccioli et al. |
| 5,766,179 A | 6/1998 | Faccioli et al. | 6,126,691 A | 10/2000 | Kasra et al. |
| 5,766,180 A | 6/1998 | Winquist | 6,127,597 A | 10/2000 | Beyar et al. |
| 5,772,662 A | 6/1998 | Chapman et al. | 6,129,756 A | 10/2000 | Kugler et al. |
| 5,776,194 A | 7/1998 | Mikol et al. | 6,129,762 A | 10/2000 | Li |
| 5,776,204 A | 7/1998 | Noble et al. | 6,139,583 A | 10/2000 | Johnson |
| 5,779,703 A | 7/1998 | Benoist | 6,143,012 A | 11/2000 | Gausepohl |

| Patent No. | Date | Inventor(s) |
|---|---|---|
| 6,143,033 A | 11/2000 | Paul et al. |
| 6,162,223 A | 12/2000 | Orsak et al. |
| 6,162,226 A | 12/2000 | DeCarlo, Jr. et al. |
| 6,168,632 B1 | 1/2001 | Moser et al. |
| 6,171,309 B1 | 1/2001 | Huebner |
| 6,176,871 B1 | 1/2001 | Pathak et al. |
| 6,179,839 B1 | 1/2001 | Weiss et al. |
| 6,179,842 B1 | 1/2001 | Spotomo et al. |
| 6,197,029 B1 | 3/2001 | Fujimori et al. |
| 6,197,031 B1 | 3/2001 | Barrette et al. |
| 6,200,321 B1 | 3/2001 | Orbay et al. |
| 6,206,880 B1 | 3/2001 | Karladani |
| 6,221,036 B1 | 4/2001 | Lucas |
| 6,221,074 B1 | 4/2001 | Cole et al. |
| 6,224,600 B1 | 5/2001 | Protogirou |
| 6,224,609 B1 | 5/2001 | Ressemann et al. |
| 6,228,123 B1 | 5/2001 | Dezzani |
| 6,231,576 B1 | 5/2001 | Frigg et al. |
| 6,235,029 B1 | 5/2001 | Faccioli et al. |
| 6,261,289 B1 | 7/2001 | Levy |
| 6,270,499 B1 | 8/2001 | Leu et al. |
| 6,273,876 B1 | 8/2001 | Klima et al. |
| 6,273,892 B1 | 8/2001 | Orbay et al. |
| 6,280,474 B1 | 8/2001 | Cassidy et al. |
| 6,283,969 B1 | 9/2001 | Grusin et al. |
| 6,287,310 B1 | 9/2001 | Fox |
| 6,290,725 B1 | 9/2001 | Weiss et al. |
| 6,296,603 B1 | 10/2001 | Turnlund et al. |
| 6,296,645 B1 | 10/2001 | Hover et al. |
| 6,299,642 B1 | 10/2001 | Chan |
| 6,319,253 B1 | 11/2001 | Ackeret et al. |
| 6,332,886 B1 | 12/2001 | Green et al. |
| 6,336,929 B1 | 1/2002 | Justin |
| 6,348,053 B1 | 2/2002 | Cachia |
| 6,355,042 B2 | 3/2002 | Winquist et al. |
| 6,355,069 B1 | 3/2002 | DeCarlo et al. |
| 6,358,250 B1 | 3/2002 | Orbay |
| 6,358,283 B1 | 3/2002 | Hogfors et al. |
| 6,364,824 B1 | 4/2002 | Fitzsimmons |
| 6,364,882 B1 | 4/2002 | Orbay |
| 6,379,359 B1 | 4/2002 | Dahners |
| 6,379,360 B1 | 4/2002 | Ackeret et al. |
| 6,383,188 B2 | 5/2002 | Kuslich et al. |
| 6,395,004 B1 | 5/2002 | Dye et al. |
| 6,402,753 B1 | 6/2002 | Cole et al. |
| 6,406,477 B1 | 6/2002 | Fujiwara |
| 6,416,516 B1 | 7/2002 | Stauch et al. |
| 6,423,096 B1 | 7/2002 | Musset et al. |
| 6,425,923 B1 | 7/2002 | Stalcup et al. |
| 6,436,148 B1 | 8/2002 | DeCarlo, Jr. et al. |
| 6,440,135 B2 | 8/2002 | Orbay et al. |
| 6,443,954 B1 | 9/2002 | Bramlet et al. |
| 6,443,992 B2 | 9/2002 | Lubinus |
| 6,447,513 B1 | 9/2002 | Griggs |
| 6,447,514 B1 | 9/2002 | Stalcup et al. |
| 6,447,515 B1 | 9/2002 | Meldrum |
| 6,447,518 B1 | 9/2002 | Krause et al. |
| 6,461,358 B1 | 10/2002 | Faccioli |
| 6,461,360 B1 | 10/2002 | Adam |
| 6,468,278 B1 | 10/2002 | Muckter |
| 6,488,684 B2 | 12/2002 | Bramlet et al. |
| 6,491,694 B1 | 12/2002 | Orsak |
| 6,500,209 B1 | 12/2002 | Kolb |
| 6,508,819 B1 | 1/2003 | Orbay |
| 6,508,820 B2 | 1/2003 | Bales |
| 6,511,481 B2 | 1/2003 | von Hoffmann et al. |
| 6,520,994 B2 | 2/2003 | Nogarin |
| 6,524,313 B1 | 2/2003 | Fassier et al. |
| 6,527,775 B1 | 3/2003 | Warburton |
| 6,530,925 B2 | 3/2003 | Boudard et al. |
| 6,533,788 B1 | 3/2003 | Orbay |
| 6,537,275 B2 | 3/2003 | Venturini et al. |
| 6,540,752 B1 | 4/2003 | Hicken et al. |
| 6,551,321 B1 | 4/2003 | Burkinshaw et al. |
| 6,554,833 B2 | 4/2003 | Levy et al. |
| 6,554,862 B2 | 4/2003 | Hays et al. |
| 6,558,388 B1 | 5/2003 | Bartsch et al. |
| 6,562,042 B2 | 5/2003 | Nelson |
| 6,565,573 B1 | 5/2003 | Ferrante et al. |
| 6,572,620 B1 | 6/2003 | Schon et al. |
| 6,575,973 B1 | 6/2003 | Shekalim |
| 6,575,986 B2 | 6/2003 | Overaker |
| 6,575,994 B1 | 6/2003 | Marin et al. |
| 6,582,453 B1 | 6/2003 | Tran et al. |
| 6,607,531 B2 | 8/2003 | Frigg |
| 6,613,052 B1 | 9/2003 | Kinnett |
| 6,616,742 B2 | 9/2003 | Lin et al. |
| 6,620,197 B2 | 9/2003 | Maroney |
| 6,623,487 B1 | 9/2003 | Goshert |
| 6,629,976 B1 | 10/2003 | Gnos et al. |
| 6,632,224 B2 | 10/2003 | Cachia et al. |
| 6,641,596 B1 | 11/2003 | Lizardi |
| 6,648,889 B2 | 11/2003 | Bramlet et al. |
| 6,648,890 B2 | 11/2003 | Culbert et al. |
| 6,652,529 B2 | 11/2003 | Swanson |
| 6,652,591 B2 | 11/2003 | Serbousek et al. |
| 6,656,189 B1 | 12/2003 | Wilson et al. |
| 6,682,568 B2 | 1/2004 | Despres, III et al. |
| 6,685,679 B2 | 2/2004 | Merdan |
| 6,685,706 B2 | 2/2004 | Padget et al. |
| 6,688,822 B2 | 2/2004 | Ritter et al. |
| 6,695,844 B2 | 2/2004 | Bramlet et al. |
| 6,699,251 B1 | 3/2004 | Venturini |
| 6,699,253 B2 | 3/2004 | McDowell et al. |
| 6,706,046 B2 | 3/2004 | Orbay et al. |
| 6,706,072 B2 | 3/2004 | Dwyer et al. |
| 6,709,436 B1 | 3/2004 | Hover et al. |
| 6,712,820 B2 | 3/2004 | Orbay |
| 6,722,368 B1 | 4/2004 | Shaikh |
| 6,723,129 B2 | 4/2004 | Dwyer et al. |
| 6,730,087 B1 | 5/2004 | Butsch |
| 6,730,090 B2 | 5/2004 | Orbay et al. |
| 6,736,818 B2 | 5/2004 | Perren et al. |
| 6,749,611 B2 | 6/2004 | Venturini et al. |
| 6,755,831 B2 | 6/2004 | Putnam et al. |
| 6,755,862 B2 | 6/2004 | Keynan |
| 6,755,866 B2 | 6/2004 | Southworth |
| 6,767,350 B1 | 7/2004 | Lob |
| 6,767,351 B2 | 7/2004 | Orbay et al. |
| 6,780,185 B2 | 8/2004 | Frei et al. |
| 6,783,529 B2 | 8/2004 | Hover et al. |
| 6,783,530 B1 | 8/2004 | Levy |
| 6,783,533 B2 | 8/2004 | Green et al. |
| 6,786,908 B2 | 9/2004 | Hover et al. |
| 6,793,655 B2 | 9/2004 | Orsak |
| 6,793,659 B2 | 9/2004 | Putnam |
| 6,808,527 B2 | 10/2004 | Lower et al. |
| 6,821,299 B2 | 11/2004 | Kirking et al. |
| 6,827,739 B2 | 12/2004 | Griner et al. |
| 6,827,741 B2 | 12/2004 | Reeder |
| 6,840,939 B2 | 1/2005 | Venturini et al. |
| 6,855,146 B2 | 2/2005 | Frigg et al. |
| 6,855,167 B2 | 2/2005 | Shimp et al. |
| 6,863,692 B2 | 3/2005 | Meulink |
| 6,866,455 B2 | 3/2005 | Hasler |
| 6,866,665 B2 | 3/2005 | Orbay |
| 6,887,243 B2 | 5/2005 | Culbert |
| 6,887,271 B2 | 5/2005 | Justin et al. |
| 6,890,333 B2 | 5/2005 | von Hoffmann et al. |
| 6,893,444 B2 | 5/2005 | Orbay |
| 6,908,465 B2 | 6/2005 | von Hoffmann et al. |
| 6,926,720 B2 | 8/2005 | Castaneda |
| 6,926,741 B2 | 8/2005 | Kolb |
| 6,929,692 B2 | 8/2005 | Tas |
| 6,942,666 B2 | 9/2005 | Overaker et al. |
| 6,942,668 B2 | 9/2005 | Padget et al. |
| 6,949,100 B1 | 9/2005 | Venturini |
| 6,949,124 B2 | 9/2005 | Serbousek et al. |
| 6,951,561 B2 | 10/2005 | Warren et al. |
| 6,974,482 B2 | 12/2005 | Zhu |
| 7,001,388 B2 | 2/2006 | Orbay et al. |
| D518,174 S | 3/2006 | Venturini et al. |
| 7,008,425 B2 | 3/2006 | Phillips |
| 7,008,428 B2 | 3/2006 | Cachia et al. |
| 7,008,451 B2 | 3/2006 | Justin et al. |
| 7,011,664 B2 | 3/2006 | Haney et al. |
| 7,012,106 B2 | 3/2006 | Yuan et al. |
| 7,029,476 B2 | 4/2006 | Hansson |

| Patent/Pub No. | Date | Name |
|---|---|---|
| 7,029,478 B2 | 4/2006 | Hollstien et al. |
| 7,033,363 B2 | 4/2006 | Powell |
| 7,033,365 B2 | 4/2006 | Powell et al. |
| 7,041,104 B1 | 5/2006 | Cole et al. |
| 7,044,978 B2 | 5/2006 | Howie et al. |
| 7,052,498 B2 | 5/2006 | Levy et al. |
| 7,056,322 B2 | 6/2006 | Davison et al. |
| 7,060,075 B2 | 6/2006 | Govari et al. |
| 7,070,601 B2 | 7/2006 | Culbert et al. |
| 7,070,616 B2 | 7/2006 | Majercak et al. |
| 7,074,224 B2 | 7/2006 | Daniels et al. |
| 7,081,119 B2 | 7/2006 | Stihl |
| 7,083,624 B2 | 8/2006 | Irving |
| 7,090,676 B2 | 8/2006 | Huebner et al. |
| 7,097,648 B1 | 8/2006 | Globerman et al. |
| 7,097,664 B2 | 8/2006 | Despres, III et al. |
| RE39,301 E | 9/2006 | Bertin |
| 7,101,376 B2 | 9/2006 | Semet |
| 7,118,574 B2 | 10/2006 | Patel et al. |
| 7,122,056 B2 | 10/2006 | Dwyer et al. |
| 7,137,987 B2 | 11/2006 | Patterson et al. |
| 7,141,052 B2 | 11/2006 | Manderson |
| 7,141,067 B2 | 11/2006 | Jones et al. |
| 7,144,399 B2 | 12/2006 | Hayes et al. |
| 7,147,639 B2 | 12/2006 | Berki et al. |
| 7,147,640 B2 | 12/2006 | Huebner et al. |
| 7,153,309 B2 | 12/2006 | Huebner et al. |
| 7,156,852 B2 | 1/2007 | Dye et al. |
| 7,160,302 B2 | 1/2007 | Warburton |
| 7,160,333 B2 | 1/2007 | Plouhar et al. |
| 7,163,563 B2 | 1/2007 | Schwartz et al. |
| 7,175,625 B2 | 2/2007 | Culbert |
| 7,175,631 B2 | 2/2007 | Wilson et al. |
| 7,179,260 B2 | 2/2007 | Gerlach et al. |
| 7,188,687 B2 | 3/2007 | Rudd et al. |
| 7,189,237 B2 | 3/2007 | Huebner |
| 7,632,277 B2 * | 12/2009 | Woll et al. ............ 606/86 R |
| 2002/0161369 A1 * | 10/2002 | Bramlet et al. .......... 606/67 |
| 2002/0188297 A1 | 12/2002 | Dakin et al. |
| 2003/0045919 A1 | 3/2003 | Swoyer et al. |
| 2003/0236529 A1 | 12/2003 | Shluzas et al. |
| 2004/0213825 A1 | 10/2004 | Levy |
| 2004/0214311 A1 | 10/2004 | Levy |
| 2004/0230193 A1 | 11/2004 | Cheung et al. |
| 2005/0015154 A1 | 1/2005 | Lindsey et al. |
| 2005/0027294 A1 | 2/2005 | Woll et al. |
| 2005/0159749 A1 | 7/2005 | Levy et al. |
| 2005/0165395 A1 | 7/2005 | Orbay et al. |
| 2005/0177158 A1 * | 8/2005 | Doubler et al. .......... 606/64 |
| 2005/0216007 A1 | 9/2005 | Woll et al. |
| 2005/0228391 A1 | 10/2005 | Levy et al. |
| 2005/0261781 A1 | 11/2005 | Sennett et al. |
| 2005/0267481 A1 | 12/2005 | Carl et al. |
| 2006/0015101 A1 | 1/2006 | Warburton et al. |
| 2006/0015123 A1 | 1/2006 | Fencl et al. |
| 2006/0064094 A1 | 3/2006 | Levy et al. |
| 2006/0084998 A1 | 4/2006 | Levy et al. |
| 2006/0200143 A1 | 9/2006 | Warburton |
| 2006/0200144 A1 | 9/2006 | Warburton |
| 2006/0229617 A1 | 10/2006 | Meller et al. |
| 2006/0264950 A1 | 11/2006 | Nelson et al. |
| 2006/0264951 A1 | 11/2006 | Nelson et al. |
| 2006/0264952 A1 | 11/2006 | Nelson et al. |
| 2008/0132896 A1 | 6/2008 | Bowen et al. |
| 2008/0140078 A1 | 6/2008 | Nelson et al. |
| 2008/0149115 A1 | 6/2008 | Hauck et al. |
| 2008/0161805 A1 | 7/2008 | Saravia et al. |
| 2008/0221620 A1 | 9/2008 | Krause et al. |
| 2009/0018542 A1 | 1/2009 | Saravia et al. |
| 2009/0228007 A1 * | 9/2009 | Justin et al. ............ 606/62 |
| 2010/0023010 A1 | 1/2010 | Nelson et al. |
| 2010/0094347 A1 | 4/2010 | Nelson et al. |

FOREIGN PATENT DOCUMENTS

| | | |
|---|---|---|
| WO | WO 97/18769 A1 | 5/1997 |
| WO | WO 98/27876 A1 | 7/1998 |
| WO | WO 98/56301 A1 | 12/1998 |
| WO | WO 99/20195 A1 | 4/1999 |
| WO | WO 00/28906 A1 | 5/2000 |
| WO | WO 01/28443 A1 | 4/2001 |
| WO | WO 02/00270 A1 | 1/2002 |
| WO | WO 02/00275 A1 | 1/2002 |
| WO | WO 02/02158 A1 | 1/2002 |
| WO | WO 2005/112804 A1 | 12/2005 |
| WO | WO 2006/053210 A1 | 5/2006 |
| WO | WO 2006/124764 A1 | 11/2006 |

OTHER PUBLICATIONS

Nelson, Charles; U.S. Appl. No. 11/565,521 entitled "Deployable intramedullary stent system for reinforcement of bone," filed Nov. 30, 2006.

Saravia et al.; U.S. Appl. No. 11/944,366 entitled "Fracture fixation device, tools and methods," filed Nov. 21, 2007.

Nelson et al.; U.S. Appl. No. 11/944,379 entitled "Surgical tools for use in deploying bone repair devices," filed Nov. 21, 2007.

Bowen et al.; U.S. Appl. No. 11/944,381 entitled "Curved orthopedic tool," filed Nov. 21, 2007.

Hauck et al.; U.S. Appl. No. 11/944,385 entitled "Surgical station for orthopedic reconstruction surgery," filed Nov. 21, 2007.

The Titanium Flexible Humeral Nail System (Quick reference for surgical technique), Synthes, 1999.

The Titanium Flexible Humeral Nail System (Technique Guide), Synthes, 1999.

Saravia et al.; U.S. Appl. No. 12/172,146 entitled "Fracture fixation device, systems and methods incorporating a membrane," filed Jul. 11, 2008.

Andermahr et al., "Anatomy of the clavicle and the intramedullary nailing of midclavicular fractures," Clinical Anatomy; vol. 20; pp. 48-56; 2007.

US 6,030,385, 02/2000, Faccioli et al. (withdrawn)

* cited by examiner

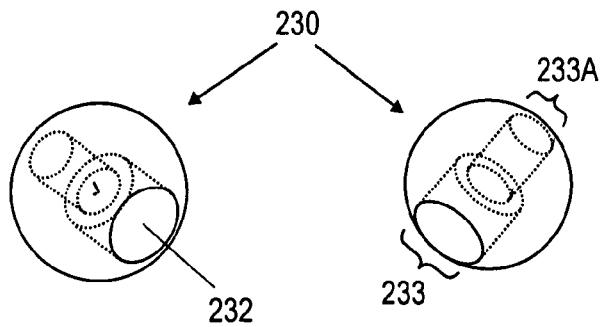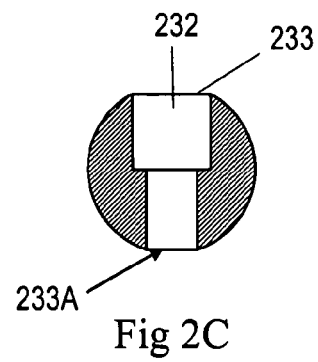
Fig 2A    Fig 2B    Fig 2C
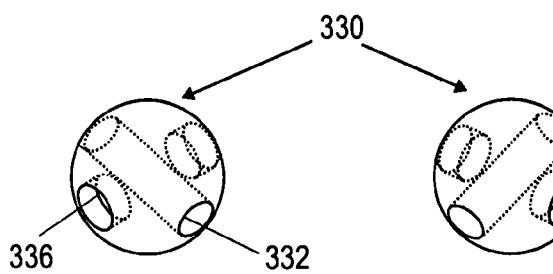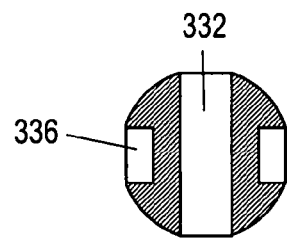
Fig 3A    Fig 3B    Fig 3C
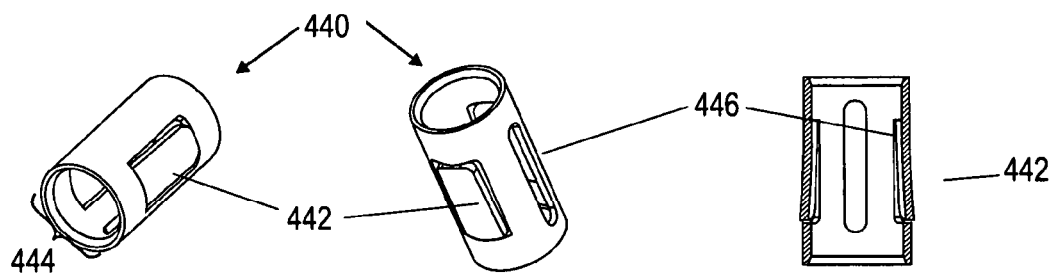
Fig 4A    Fig 4B    Fig 4C
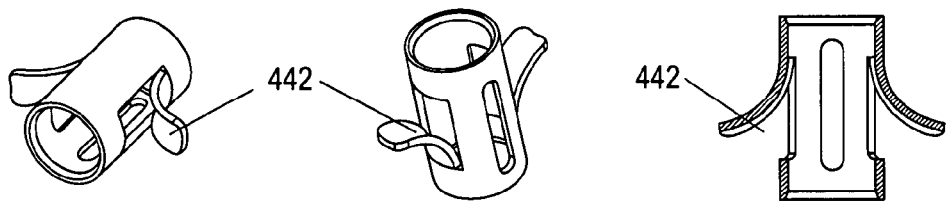
Fig 4D    Fig 4E    Fig 4F

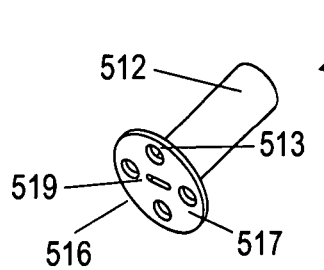 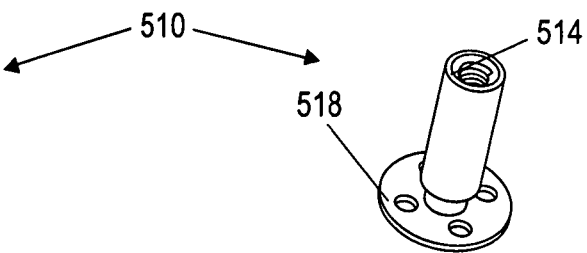
Fig. 5A　　　　　　　Fig. 5B
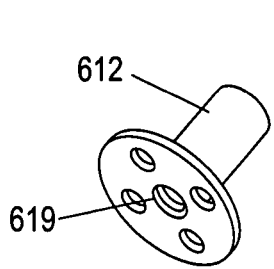 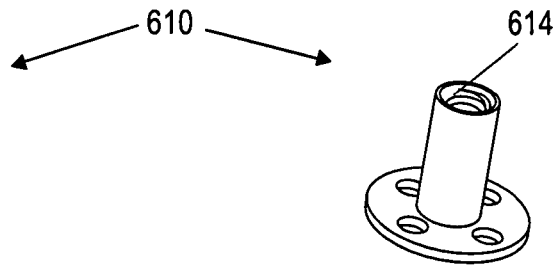
Fig. 6A　　　　　　　Fig. 6B
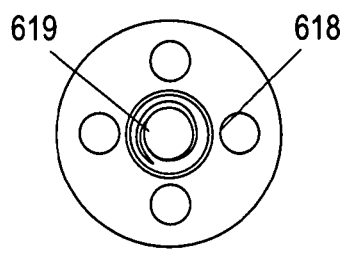 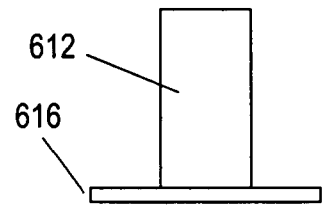
Fig. 6C　　　　　　　Fig. 6D
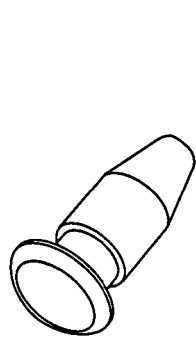 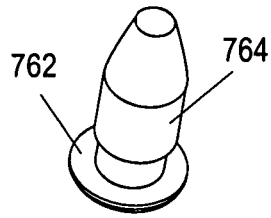 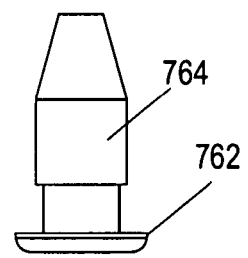
Fig. 7A　　　Fig. 7B　　　Fig. 7C

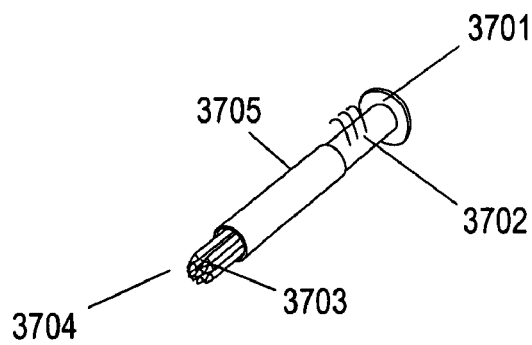
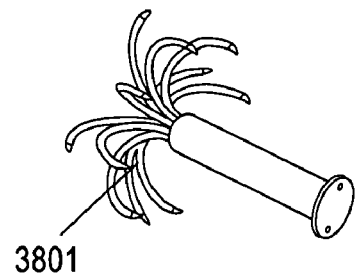
Fig 37
Fig 38
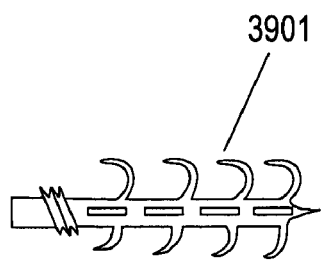
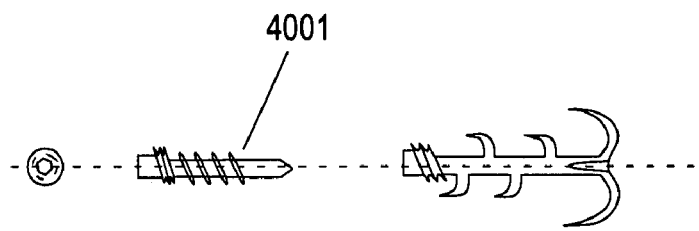
Fig 39
Fig 40
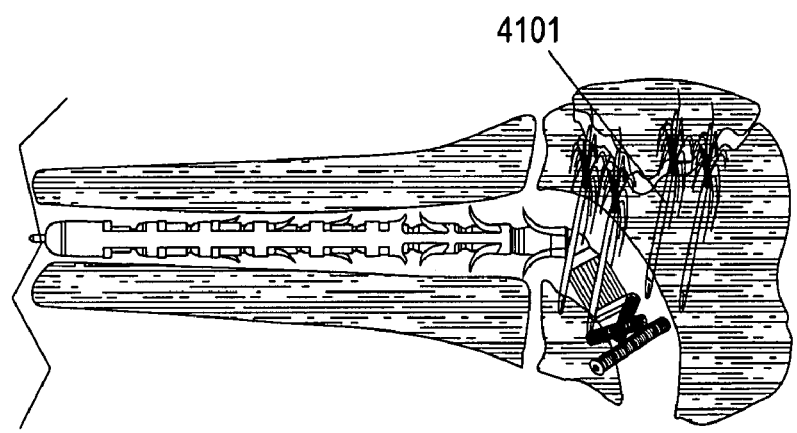
Fig 41

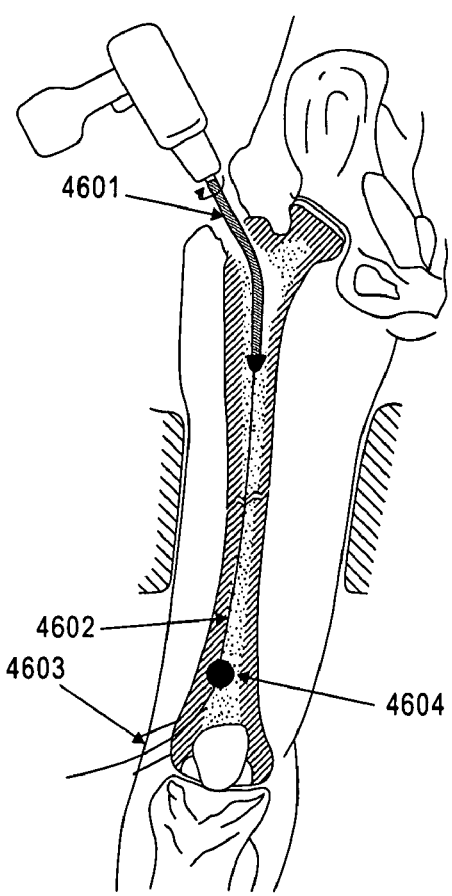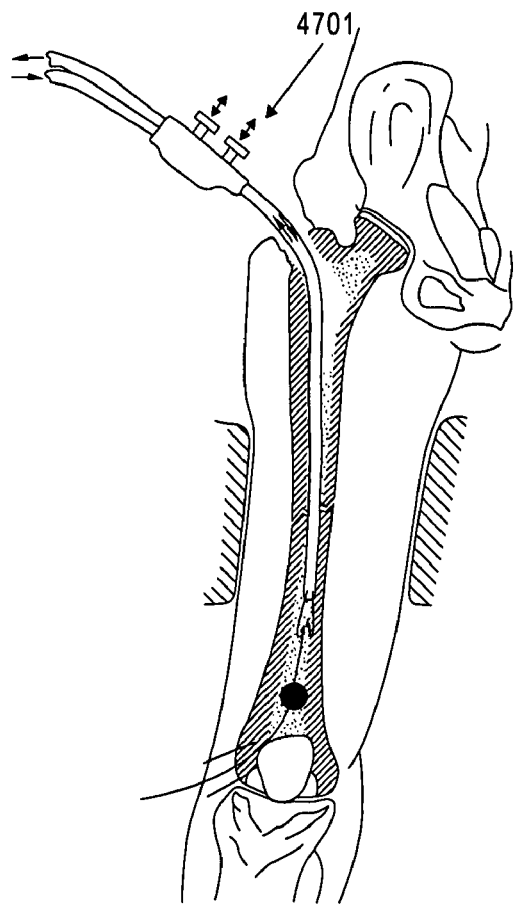
Fig. 46        Fig. 47
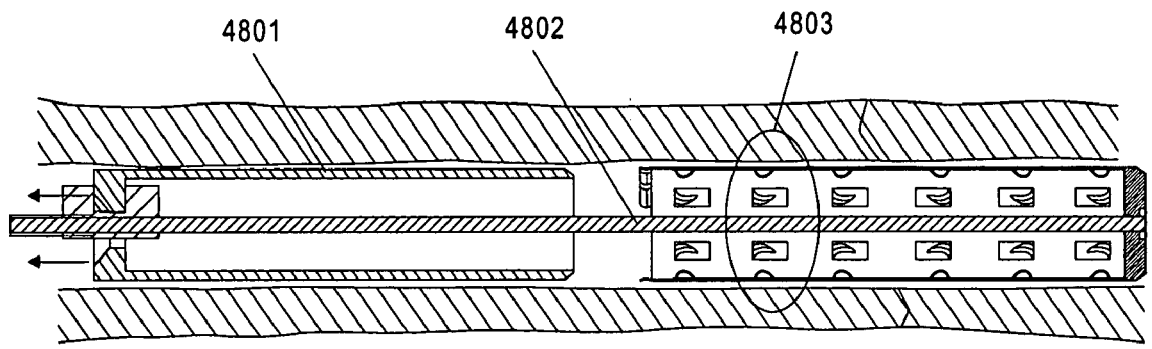
Fig. 48

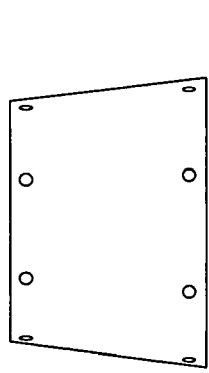
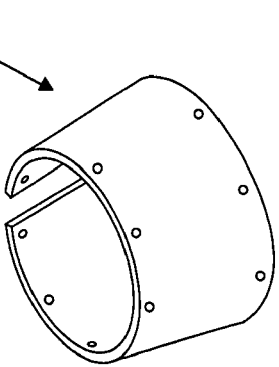
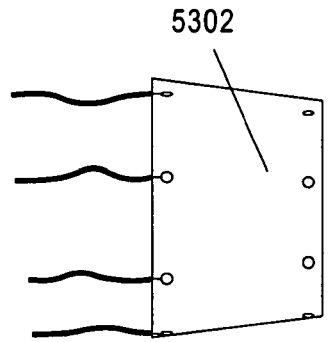
Fig. 53A　　　　　Fig. 53B　　　　　Fig. 53C
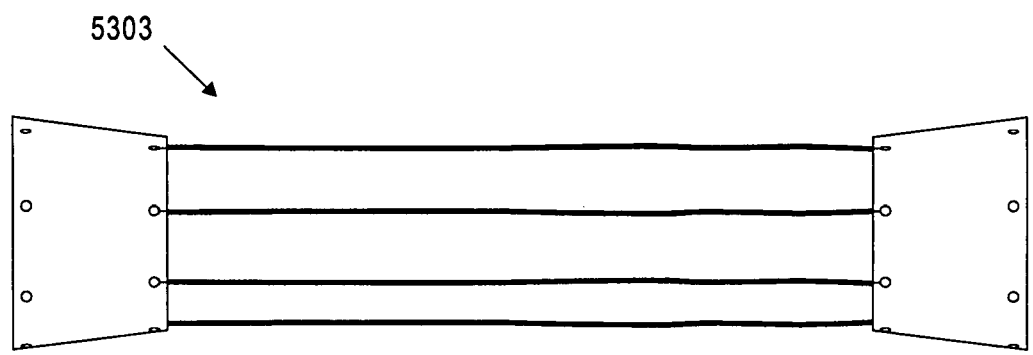
Fig. 53D
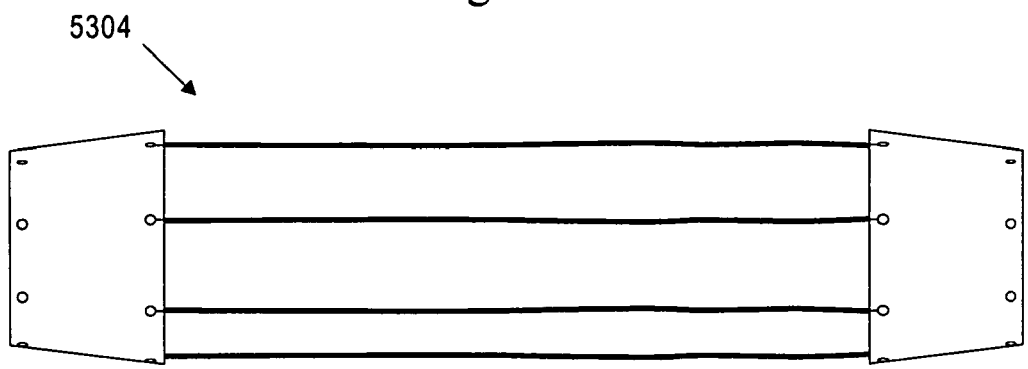
Fig. 53E

MINIMALLY INVASIVE ACTUABLE BONE FIXATION DEVICES

CROSS-REFERENCE

This application is a continuation application of Ser. No. 11/383,269, filed May 15, 2006 by Nelson entitled Minimally Invasive Actuable Bone Fixation Devices, to which application priority under 35 USC §120 is claimed, and which claims the benefit of U.S. Provisional Application No. 60/682,652, filed May 18, 2005 entitled Method and System for Providing Reinforcement of Bones, each of which are incorporated herein by reference in their entirety.

BACKGROUND OF THE INVENTION

The present invention relates to method and system for providing reinforcement of bones. More specifically, the present invention relates to method and system for providing reconstructive surgical procedures and devices for reconstruction and reinforcement bones, including diseased, osteoporotic and fractured bones.

Bone fractures are a common medical condition both in the young and old segments of the population. However, with an increasingly aging population, osteoporosis has become more of a significant medical concern in part due to the risk of osteoporotic fractures. Osteoporosis and osteoarthritis are among the most common conditions to affect the musculoskeletal system, as well as frequent causes of locomotor pain and disability. Osteoporosis can occur in both human and animal subjects (e.g. horses). Osteoporosis (OP) and osteoarthritis (OA) occur in a substantial portion of the human population over the age of fifty. The National Osteoporosis Foundation estimates that as many as 44 million Americans are affected by osteoporosis and low bone mass, leading to fractures in more than 300,000 people over the age of 65. In 1997 the estimated cost for osteoporosis related fractures was $13 billion. That figure increased to $17 billion in 2002 and is projected to increase to $210-240 billion by 2040. Currently it is expected that one in two women, and one in four men, over the age of 50 will suffer an osteoporosis-related fracture. Osteoporosis is the most important underlying cause of fracture in the elderly.

One current treatment of bone fractures includes surgically resetting the fractured bone. After the surgical procedure, the fractured area of the body (i.e., where the fractured bone is located) is often placed in an external cast for an extended period of time to ensure that the fractured bone heals properly. This can take several months for the bone to heal and for the patient to remove the cast before resuming normal activities.

In some instances, an intramedullary (IM) rod or nail is used to align and stabilize the fracture. In that instance, a metal rod is placed inside a canal of a bone and fixed in place, typically at both ends. See, for example, Fixion™ IM (Nail), www.disc-o-tech.com. This approach requires incision, access to the canal, and placement of the IM nail. The nail can be subsequently removed or left in place. A conventional IM nail procedure requires a similar, but possibly larger, opening to the space, a long metallic nail being placed across the fracture, and either subsequent removal, and or when the nail is not removed, a long term implant of the IM nail. The outer diameter of the IM nail must be selected for the minimum inside diameter of the space. Therefore, portions of the IM nail may not be in contact with the canal. Further, micromotion between the bone and the IM nail may cause pain or necrosis of the bone. In still other cases, infection can occur. The IM nail may be removed after the fracture has healed. This requires a subsequent surgery with all of the complications and risks of a later intrusive procedure.

External fixation is another technique employed to repair fractures. In this approach, a rod may traverse the fracture site outside of the epidermis. The rod is attached to the bone with trans-dermal screws. If external fixation is used, the patient will have multiple incisions, screws, and trans-dermal infection paths. Furthermore, the external fixation is cosmetically intrusive, bulky, and prone to painful inadvertent manipulation by environmental conditions such as, for example, bumping into objects and laying on the device.

Other concepts relating to bone repair are disclosed in, for example, U.S. Pat. No. 5,108,404 to Scholten for Surgical Protocol for Fixation of Bone Using Inflatable Device; U.S. Pat. No. 4,453,539 to Raftopoulos et al. for Expandable Intramedullary Nail for the Fixation of Bone Fractures; U.S. Pat. No. 4,854,312 to Raftopolous for Expanding Nail; U.S. Pat. No. 4,932,969 to Frey et al. for Joint Endoprosthesis; U.S. Pat. No. 5,571,189 to Kuslich for Expandable Fabric Implant for Stabilizing the Spinal Motion Segment; U.S. Pat. No. 4,522,200 to Stednitz for Adjustable Rod; U.S. Pat. No. 4,204,531 to Aginsky for Nail with Expanding Mechanism; U.S. Pat. No. 5,480,400 to Berger for Method and Device for Internal Fixation of Bone Fractures; U.S. Pat. No. 5,102,413 to Poddar for Inflatable Bone Fixation Device; U.S. Pat. No. 5,303,718 to Krajicek for Method and Device for the Osteosynthesis of Bones; U.S. Pat. No. 6,358,283 to Hogfors et al. for Implantable Device for Lengthening and Correcting Malpositions of Skeletal Bones; U.S. Pat. No. 6,127,597 to Beyar et al. for Systems for Percutaneous Bone and Spinal Stabilization, Fixation and Repair; U.S. Pat. No. 6,527,775 to Warburton for Interlocking Fixation Device for the Distal Radius; U.S. Patent Publication US2006/0084998 A1 to Levy et al. for Expandable Orthopedic Device; and PCT Publication WO 2005/112804 A1 to Myers Surgical Solutions, LLC for Fracture Fixation and Site Stabilization System.

In view of the foregoing, it would be desirable to have a device, system and method for providing effective and minimally invasive bone reinforcement to treat fractured or diseased bones.

SUMMARY OF THE INVENTION

One embodiment of the present invention provides a low weight to volume mechanical support for fixation, reinforcement and reconstruction of bone or other regions of the musculo-skeletal system. The method of delivery of the device is another aspect of the invention. The method of delivery of the device in accordance with the various embodiments of the invention reduces the trauma created during surgery, decreasing the risks associated with infection and thereby decreasing the recuperation time of the patient. The framework may in one embodiment include an expandable and contractable structure to permit re-placement and removal of the reinforcement structure or framework.

In accordance with the various embodiments of the present invention, the mechanical supporting framework or device may be made from a variety of materials such as metal, composite, plastic or amorphous materials, which include, but are not limited to, steel, stainless steel, cobalt chromium plated steel, titanium, nickel titanium alloy (nitinol), super elastic alloy, and polymethylmethacrylate (PMMA). The supporting framework or device may also include other polymeric materials that are biocompatible and provide mechanical strength, that include polymeric material with ability to carry and delivery therapeutic agents, that include bioabsorbable properties, as well as composite materials and composite materials of titanium and polyetheretherketone (PEEK™), composite materials of polymers and minerals, composite materials of polymers and glass fibers, composite materials of metal, polymer, and minerals.

Within the scope of the present invention, each of the aforementioned types of device may further be coated with proteins from synthetic or animal source, or include collagen coated structures, and radioactive or brachytherapy materials. Furthermore, the construction of the supporting framework or device may include radio-opaque markers or components that assist in their location during and after placement in the bone or other region of the musculo-skeletal systems.

Further, the reinforcement device may, in one embodiment, be osteo incorporating, such that the reinforcement device may be integrated into the bone.

In a further embodiment, there is provided a low weight to volume mechanical supporting framework or device deployed in conjunction with other suitable materials to form a composite structure in-situ. Examples of such suitable materials may include, but are not limited to, bone cement, high density polyethylene, Kapton®, polyetheretherketone (PEEK™), and other engineering polymers.

Once deployed, the supporting framework or device may be electrically, thermally, or mechanically passive or active at the deployed site within the body. Thus, for example, where the supporting framework or device includes nitinol, the shape of the device may be dynamically modified using thermal, electrical or mechanical manipulation. For example, the nitinol device or supporting framework may be expanded or contracted once deployed, to move the bone or other region of the musculo-skeletal system or area of the anatomy by using one or more of thermal, electrical or mechanical approaches.

An embodiment of the invention includes a lockable bone fixation device comprising: a sleeve adapted to be positioned in a space formed in a bone; a guidewire adapted to guide movement of the sleeve; and an actuable lock adapted to secure the sleeve within the space of the bone from an end of the device. The sleeve can be configured to be flexible, have apertures, be expandable and/or be bioabsorbable. Further, the sleeve can be removable from the space within the bone, if desired. The device is adapted and configured to access the space within the bone through an access aperture formed in a bony protuberance of the bone. In a further embodiment, a second sleeve can be provided that is adapted to fit within the first sleeve. Where a second sleeve is provided, the second sleeve can be used to control a retractable interdigitation process or teeth. The sleeve can accomplish this control by being configured with slots or apertures along its length through which the teeth extend when the slots are positioned over the teeth. Once the teeth are exposed through the second sleeve, the teeth or interdigitation process are adapted to engage bone. In still another embodiment of the invention, a cantilever adapted to retain the lockable bone fixation device within the space. Another embodiment of the invention includes adapting the sleeve to be expanded and collapsed within the space by a user. In still another embodiment, the device is adapted to be delivered by a catheter. In yet another embodiment, the distal end of the device is adapted to provide a blunt obdurator surface. In still another embodiment of the device, the distal end of the device is configured to provide a guiding tip. In yet another embodiment of the device, the device is adapted to receive external stimulation to provide therapy to the bone. In still another embodiment of the device, the device is adapted to receive composite material when the device is disposed within a lumen or opening within the body or bone.

In another embodiment of the invention, a bone fixation device is provided that comprises: a first sleeve having a retractable interdigitation process at a location along its length adapted to engage a bone; and a second sleeve sized adapted to activate the interdigitation process of the first sleeve. The bone fixation device can be configured to provide a flexible first or second sleeve. In another embodiment, the first or second sleeve can be provided with apertures, can be expandable and/or can be fashioned from bioabsorbable materials. In still other embodiments, either of the first or second sleeve can be removable. In yet another embodiment of the invention, the first and second sleeve are adapted to access a space of the bone through an access aperture formed in a bony protuberance of the bone. In still other embodiments, the second sleeve can be configured to provide a retractable interdigitation process or teeth. Apertures can also be provided in some embodiments, along the length of the device through which the retractable interdigitation process engages the bone. The apertures can, in some embodiments, be on the second sleeve. In some embodiments, the retractable interdigitation process can be adapted to engage bone when actuated by the second sleeve. In still other embodiments, a cantilever retains the bone fixation device within a space of the bone. Further, a first or second sleeve is adapted in some embodiments to be expanded and collapsed within the bone by a user. In still other embodiments, the device is adapted to be delivered by a catheter or catheter-like device. The catheter may be a single or multilumen tube. The catheter may employ methods or apparatus that power or shape the device for introduction and placement. The distal end of the device in some embodiments is adapted to provide a blunt obdurator surface. Additionally, the distal end of the device can have a guiding tip. In still other embodiments, the device is adapted to deliver therapeutic stimulation to the bone. In other embodiments the device is adapted to deliver therapeutic stimulation to the biological processes within bone. These processes are cellular in nature and provide therapeutic remedies to the health of the patient not related to bone. One such therapeutic application is anemia or hemophilia. In yet other embodiments, the device is adapted to receive composite material when the device is disposed within a lumen.

In still another embodiment of the invention, a method of repairing a bone fracture is disclosed that comprises: accessing a fracture along a length of a bone through a bony protuberance at an access point at an end of a bone; advancing a bone fixation device into a space through the access point at the end of the bone; bending a portion of the bone fixation device along its length to traverse the fracture; and locking the bone fixation device into place within the space of the bone. The method can also include the step of advancing an obdurator through the bony protuberance and across the fracture prior to advancing the bone fixation device into the space. In yet another embodiment of the method, the step of anchoring the bone fixation device within the space can be included. In still another embodiment of the method, a first sleeve and a second sleeve of the bone fixation device can be engaged to expand an interdigitation process into the bone.

An aspect of the invention discloses a removable bone fixation device that has a single end of introduction, deployment, and remote actuation wherein a bone fixation device stabilizes bone. The bone fixation device is adapted to provide a single end in one area or location where the device initiates interaction with bone. The device can be deployed such that the device interacts with bone. Remote actuation activates, deactivates, reduces bone, displaces bone, locks, places, removes, grips, stiffens device, compresses, adjusts, axially adjusts, torsionally adjusts, angularly adjusts, and releases the devices during its interaction with bone. A removable extractor can be provided in some embodiments of the device to enable the device to be placed and extracted by deployment and remote actuation from a single end. The device of the invention can be adapted and configured to provide at least one sleeve. Further the sleeve can be configured to be flexible in all angles and directions. The flexibility provided is in selective planes and angles in the Cartesian, polar, or cylindrical coordinate systems. Further, in some embodiments, the sleeve is configured to have a remote actuation at a single end. Additionally, the sleeve can be configured to have apertures. In still further embodiments, the sleeve is configured to minimize boney in-growth. Another aspect of the invention includes a bone fixation device in that has mechanical geometry that interacts with bone by a change in the size of at least one dimension of a Cartesian, polar, or spherical coordinate system. Further, in some embodiments, bioabsorbable materials can be used in conjunction with the devices, for example by providing specific subcomponents of the device configured from bioabsorbable materials. A second sleeve can be provided in some embodiments where the second sleeve is removable, has deployment, remote actuation, and a single end. Where a second sleeve is employed, the second sleeve can be adapted to provide a deployable interdigitation process or to provide an aperture along its length through which the deployable interdigitation process is adapted to engage bone. In some embodiments, the deployable interdigitation process is further adapted to engage bone when actuated by the sleeve. In some embodiments, the bone fixation device further comprises a cantilever adapted to retain the deployable bone fixation device within the space. The sleeve can further be adapted to be expanded and collapsed within the space by a user. One end of the device can be configured to provide a blunt obdurator surface adapted to advance into the bone. A guiding tip may also be provided that facilitates guiding the device through the bone. Further, the deployable bone fixation device can be adapted to receive external stimulation to provide therapy to the bone. The device can further be adapted to provide an integral stimulator which provides therapy to the bone. In still other embodiments, the device can be adapted to receive deliver therapeutic stimulation to the bone.

The invention also includes a method for repairing a bone fracture comprising: accessing a fracture along a length of bone through a bony protuberance at an entry portal; introducing the bone fixation device into the medullary canal through the entry portal; bending the bone fixation device along its length to advance into the medullary space in the bone; bending the bone fixation device along its length to traverse the fracture site; placing a flexible elbow in the medullary canal at the fracture site; stiffening the bone fixation device; locking the bone fixation device to the bone; reducing the fracture with the bone fixation device in place in the medullary canal; locking the flexible elbow to achieve intramedullary reduction of the fracture. The method can further include the step of introducing a guide wire into the medullary space through a bony protuberance at an entry portal. Additionally, the guidewire can be reamed through the bony protuberance at an entry portal. The location of the reamed boney canal can be determined by the fracture anatomy and bone anatomy. In some embodiments of the method, a sleeve can be advanced along the bone fixation device. In such embodiments, the sleeve can function to unlock the spikes from the fixation device. Once the spikes are unlocked from the fixation device, the spikes then fix the device to the bone. Locking butterfly rings can also be employed to lock the device to the bone. The butterfly rings can be locked to the fixation device in some embodiments. Additionally, the rings can be threaded over the device. In other embodiments, a guide jig guides screws through the butterfly rings. Further self tapping screws lock the butterfly rings to the bone and bone fixation device. A set screw can also be used to lock the device at the fracture site. The device can also be stiffened. In performing the method of the invention, fracture fragments can be reduced.

Yet another aspect of the invention includes a barb-screw comprising a sleeve, one or more teeth deployable at a distal end of the sleeve, and an actuable lock adapted to secure the sleeve within the space of the bone from an end of the device.

These and other features and advantages of the present invention will be understood upon consideration of the following detailed description of the invention and the accompanying drawings.

INCORPORATION BY REFERENCE

All publications, patents and patent applications mentioned in this specification are herein incorporated by reference in their entirety to the same extent as if each individual publication, patent or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 2A-C depict views of a bearing segment suitable for use in an actuable bone fixation device;

FIGS. 3A-C depict views of a bearing segment suitable for use in an actuable bone fixation device;

FIG. 4A-F depict a retention segment suitable for use in an actuable bone fixation device;

FIGS. 5A-B illustrate an external actuator suitable for use in an actuable bone fixation device;

FIGS. 6A-D illustrate an alternate embodiment of an external actuator suitable for use in an actuable bone fixation device;

FIGS. 7A-C illustrate a pin suitable for use in an actuable bone fixation device;

FIG. 37 illustrates An actuable barb-screw according to the invention;

FIG. 38 illustrates a deployed barb-screw;

FIG. 39 illustrates a side view of a barb-screw;

FIG. 40 depicts a two part barb-screw according to the invention;

FIG. 41 illustrates a deployed actuable bone fixation device deployed with transversely positioned actuable barb-screws;

FIG. 46 illustrates a femur with a coring reamer boring a hole in the shaft of the bone;

FIG. 47 illustrates a lavage system used with a bidirectional flow path to remove debris from within the bone;

FIG. 48 illustrates an actuable bone fixation device within a bone;

FIGS. 53A-E illustrate implantation of a plurality of structural reinforcement devices within a bone;

DETAILED DESCRIPTION OF THE INVENTION

By way of background and to provide context for the invention, it may be useful to understand that bone is often described as a specialized connective tissue that serves three major functions anatomically. First, bone provides a mechanical function by providing structure and muscular attachment for movement. Second, bone provides a metabolic function by providing a reserve for calcium and phosphate. Finally, bone provides a protective function by enclosing bone marrow and vital organs. Bones can be categorized as long bones (e.g. radius, femur, tibia and humerus) and flat bones (e.g. skull, scapula and mandible). Each bone type has a different embryological template. Further each bone type contains cortical and trabecular bone in varying proportions.

Cortical bone (compact) forms the shaft, or diaphysis, of long bones and the outer shell of flat bones. The cortical bone provides the main mechanical and protective function. The trabecular bone (cancellous) is found at the end of the long bones, or the epiphysis, and inside the cortex of flat bones. The trabecular bone consists of a network of interconnecting trabecular plates and rods and is the major site of bone remodeling and resorption for mineral homeostasis. During development, the zone of growth between the epiphysis and diaphysis is the metaphysis. Finally, woven bone, which lacks the organized structure of cortical or cancellous bone, is the first bone laid down during fracture repair. Once a bone is fractured, the bone segments are positioned in proximity to each other in a manner that enables woven bone to be laid down on the surface of the fracture. This description of anatomy and physiology is provided in order to facilitate an understanding of the invention. Persons of skill in the art, will appreciate that the scope and nature of the invention is not limited by the anatomy discussion provided. Further, it will be appreciated there can be variations in anatomical characteristics of an individual, as a result of a variety of factors, which are not described herein.

Figure 1A:
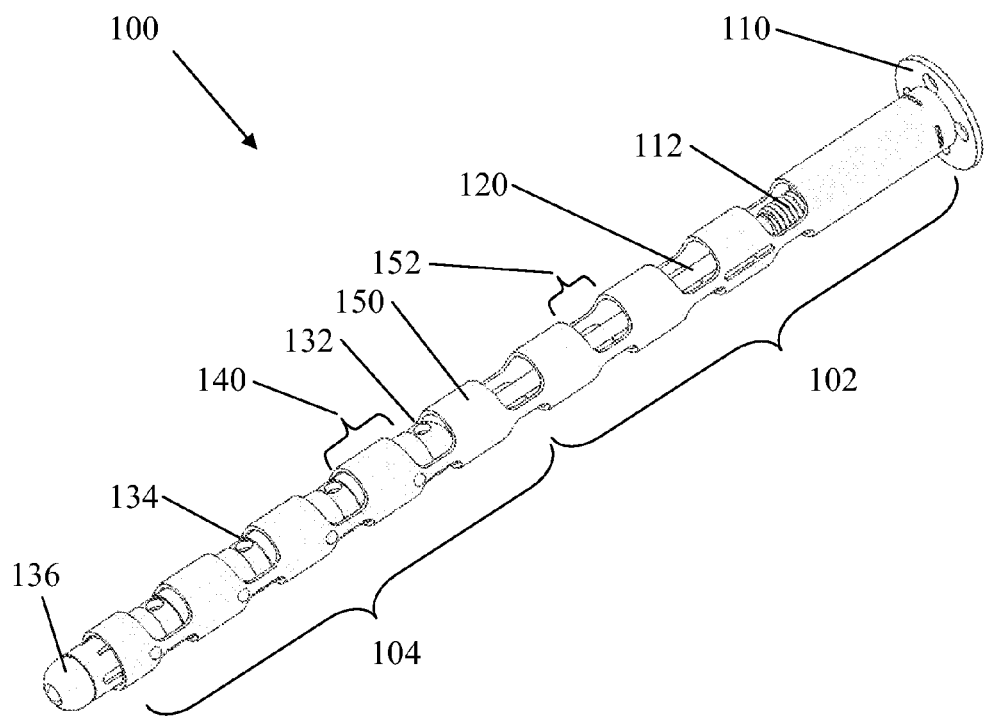
FIGS. 1A-B depict an actuable bone fixation device in a pre-deployed and deployed condition.
Figure 1B:
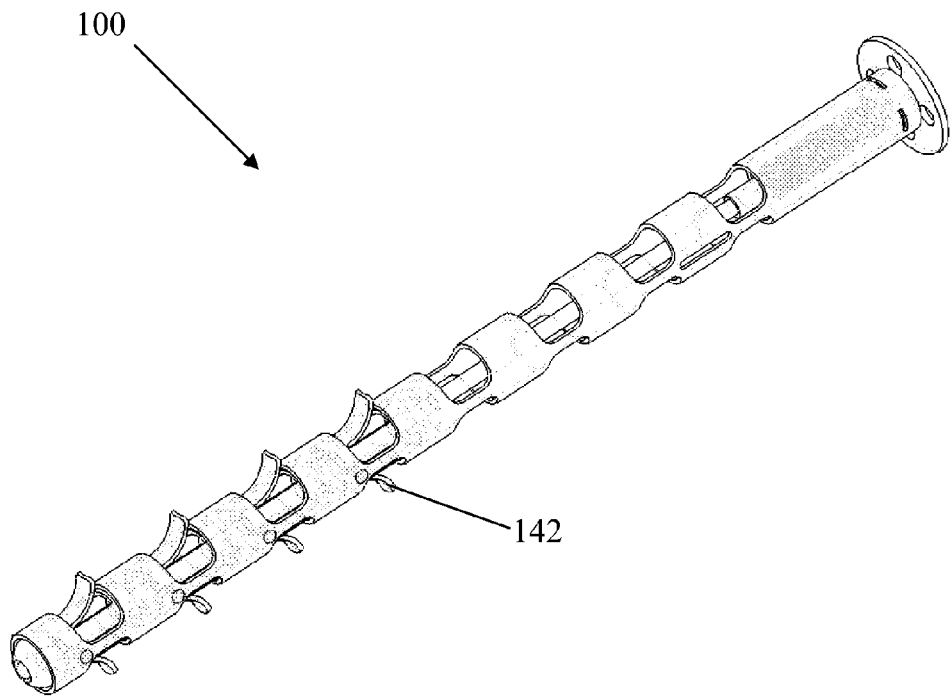

FIGS. 1A-B depict an actuable bone fixation device 100 in a pre-deployed and deployed condition. The bone fixation device 100 has a proximal end 102 and a distal end 104. The proximal end and distal end, as used in this context, refers to the position of an end of the device relative to the remainder of the device or the opposing end as it appears in the drawing. The proximal end can be used to refer to the end manipulated by the user or physician. The proximal end may be configured such that a portion thereof remains outside the bone. Alternatively, the proximal end is configured such that it does not remain outside the bone. The distal end, thus, can be used to refer to the end of the device that is inserted and advanced within the bone and is furthest away from the physician. As will be appreciated by those skilled in the art, the use of proximal and distal could change in another context, e.g. the anatomical context.

The bone fixation device is suitable for reinforcing and/or repairing a bone. Further, the bone fixation device is adapted to be anatomically conformable. Still further, the bone fixation device is adapted to cross a fracture. Once actuated, the device anchors into a portion of the bone and then draws the bone segments effected by the fracture together. Kirshner or K-wires can also be used where there are additional fracture fragments.

The bone fixation device 100 has an actuator 110 at a proximal end 102. The actuator 110 enables a user to control the movement, insertion, deployment, removal, and operation of the device. The actuator 110 has internal threads (not shown) that engage threads 112 formed on a shaft or guidewire 120. The shaft 120 extends through a proximal bearing segment 132, intermediate bearing segments 134 and terminates in a distal bearing segment 136. Interposed between the bearing segments on shaft 120 are anchoring segments 140. The bearing segments control translation and bending of the device 100. In some embodiments, the bearing segments can withstand, for example, up to 800 lb of axial loading force. The anchoring segments 140 have radially extending teeth or grippers 142 that deploy upon actuation of the device 100 to interlock the device with the bone, as explained below.

The outer sheath 150 is a component of the device 100. The outer sheath surrounds a portion of the exposed length of the device 100. Slots 152 are provided along its length that enable the teeth 142 of the anchoring segment 140 to extend radially away from the external surface of the device 100 and into the bone when the device is actuated. The slots 152 can also be adapted to promote or control bending of the device, as will be appreciated below. In FIG. 1A, the device is depicted in a pre-deployed state, i.e., prior to deploying the anchoring teeth. Prior to deployment, the teeth 142 of the anchoring segment 140 are positioned within the sleeve 150. When the device is actuated, as illustrated in FIG. 1B, the actuator 110 is rotated such that the drive shaft 120 is drawn into the actuator 110. Drawing the drive shaft 120 into the actuator pulls the bearing segments and anchoring segments proximally with respect to the sleeve 150, thus positioning the anchoring segments 140 and teeth 142 adjacent the slots 152. In this embodiment, teeth 142 are formed from an expansible material such as a shape memory alloy, such as the nitinol, to restore to an unconstrained position upon actuation of the device. This actuation results in movement of the teeth radially away from the shaft of the device. The teeth are retractable as needed or desired by reversing the direction of rotation of actuator 110, thereby pushing the bearing segments and anchoring segments distally with respect to the sleeve. The slope and angle of teeth 142 help the edge of slots 152 cam teeth 142 inward to the position shown in FIG. 1A.

FIGS. 2A-C depict views of a bearing segment 230 (see also, bearing segment 136 in FIG. 1) suitable for use in an actuable bone fixation device at, for example, the distal end. As illustrated in FIGS. 2A-B, the bearing segment, as depicted, has a substantially spherical dimension, with a lumen 232 positioned therethrough for receiving a drive shaft or guide wire, such as shown above. The lumen, as depicted, has a first circumference at a first end 233 and a second circumference 233A at a second end. First circumference, 233, is a distal circumference (as oriented during implantation) adapted and configured to accommodate a swaged or discontinuous intermediate interfering locking feature. The swaged feature prevents proximal to distal translation of the distal bearing segment, 136 of the device, thereby retaining all proximal internal components of the device 100. FIG. 2C illustrates the bearing segment in cross-section further illustrating a substantially circular external shape with a first diameter 233 corresponding to the first circumference and a second diameter 233A corresponding to the second circumference. When positioned distally, the bearing segment can function as a blunt obdurator adapted to facilitate penetration of bone.

FIGS. 3A-C depict views of another bearing segment 330 suitable for use in an actuable bone fixation device. The bearing segment, as depicted, has a substantially spherical dimension, with a lumen 332 positioned therethrough. The lumen depicted in this embodiment has a constant, or substantially constant, diameter along its length suitable for receiving the drive shaft or guide wire 120 of a device 100. Additional detents 336, indentations or lumens can be provided. The detents 336 can be configured on the surface such that the detents would be positioned on opposing sides of the bearing segment 330, as depicted, without crossing or penetrating the lumen 332 formed to receive the drive shaft. The detents can be formed to receive pins, or be formed to provide an additional lumen through the bearing segment, or compressed or swaged onto the drive shaft or can be configured in any other suitable configuration. As depicted in FIG. 3C, the lumen 332 traverses the bearing segment 330, while the detents are formed on opposing sides and oriented 90° from an axis around which the lumen 332 is positioned. Other orientations and configurations are possible without departing from the scope of the invention.

Turning now to FIG. 4A-F, a retention or anchoring segment suitable for use in an actuable bone fixation device of the invention is depicted. FIGS. 4A-B illustrate perspective views of the anchoring segment 440 prior to deployment of the teeth 442. The anchoring segment 440 is adapted to fit within the sleeve 150 (FIGS. 1A-B) and to have a central lumen 444 through which a drive shaft 120 (FIGS. 1A-B) or guidewire can be positioned. A portion of the exterior surface of the anchoring segment 440 can be configured to form one or more teeth 442. The teeth 442 can be formed integrally with the anchoring segment 440. The teeth 442 and/or the anchoring segment 440 can be formed of any suitable material, including nitinol. Where a shape memory alloy is used, the teeth 442 can be configured to assume a pre-determined shape when the teeth are not constrained within the sleeve, as shown in FIG. 4E. Additional slots 446 can be provided along the length of the anchoring segment. The slots 446 can be used to engage, for example, pins extending from the outer sleeve to control rotational movement of the anchoring segment within the sleeve. Turning to FIG. 4D-E, the teeth 442 are bent away from the exterior surface of the anchoring segment 440. FIG. 4F illustrates a cross-section of the anchoring device depicted herein wherein the teeth 442 are deflected away from the sides of the anchoring segment. The teeth may emanate from alternate surfaces and cross at the centerline of the lumen 444, thereby creating a longer cantilever segment.

FIGS. 5A-B illustrate an actuator suitable for use in an actuable bone fixation device. The actuator 510 has a cylindrical body 512 with a threaded female interior 514 or any other configuration capable of actuation for exposure of the teeth 442. A flange 516 is provided that can be used to anchor the device against a surface, such as bone. Additionally, the top surface of the flange 516 can be adapted to enable control of the actuator 510 and the drive shaft 120 shown in FIG. 1. One or more apertures 518 can be provided to engage, for example, screws. The apertures 518 can provide a mechanism to anchor the device to the surface of the bone (as opposed to just abutting the surface of the bone). The outer circumferential surface 517 of the flange 516 can further be provided with markings

513 or adapted to provide an indicator to facilitate deploying the teeth by providing an indication to the user of the relative position of the teeth relative to the slots on the sheath and relative to the plane within the bone. Thereby establishing the direction of flexibility of the device while in bone. Additionally, a central aperture 519 which forms a keyway can be provided for engaging an additional tool or device to control the deployment of the bone fixation device. For example, the central aperture 519 can be in the shape of a slit to accept, for example, the head of a flat head screw driver.

FIGS. 6A-D illustrate an alternate embodiment of an actuator 610 suitable for use in an actuable bone fixation device. In the embodiment depicted in FIGS. 6A-B, the central aperture 619 is adapted to engage a tool with a threaded end. FIGS. 6C-D illustrate a top view and side view of the actuator 610. Similar to the device depicted in FIG. 5, actuator 610 has a cylindrical body 612 with a threaded female interior 614 or any other configuration capable of actuation for exposure of the teeth 642. A flange 616 is provided that can be used to anchor the device against a surface, such as bone. Additionally, the top surface of the flange 616 can be adapted to enable control of the actuator 610 and the drive shaft 120 (shown in FIG. 1. One or more apertures 618 can be provided to engage, for example, screws. The apertures 618 can provide a mechanism to anchor the device to the surface of the bone (as opposed to abutting the surface of the bone). Additionally, a central aperture 619 which forms a keyway can be provided for engaging an additional tool or device to control the deployment of the bone fixation device. For example, the central aperture 619 can be in the shape of a slit to accept, for example, the head of a flat head screw driver.

FIGS. 7A-C illustrate a pin 760 suitable for use in an actuable bone fixation device to prevent rotational movement of the anchoring segment relative to the sheath. The pin 760 has a head 762 adapted to engage an interior portion of the sleeve and a neck 764 to fit within the slot in the anchoring mechanism.

Figures 8A, 8B:
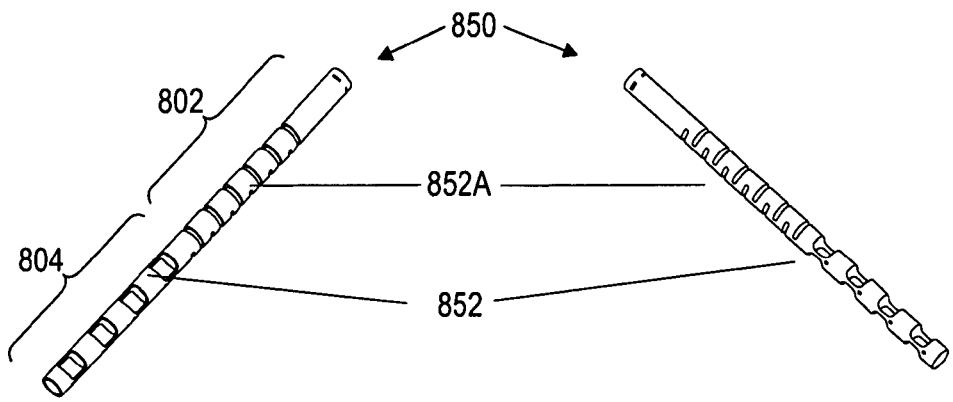
FIGS. 8A-D illustrate a configuration of an outer sleeve suitable for use in a bone fixation device.
Figures 8C, 8D:
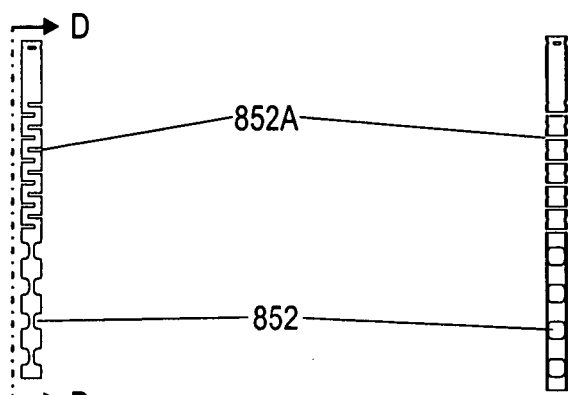
Figures 9A, 9B:
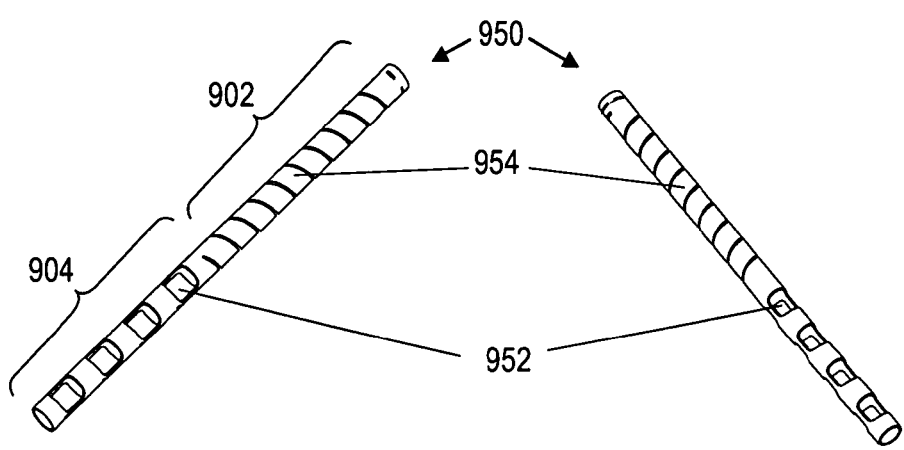
FIGS. 9A-D illustrate an alternate configuration of an outer sleeve suitable for use in a bone fixation device.
Figures 9C, 9D:
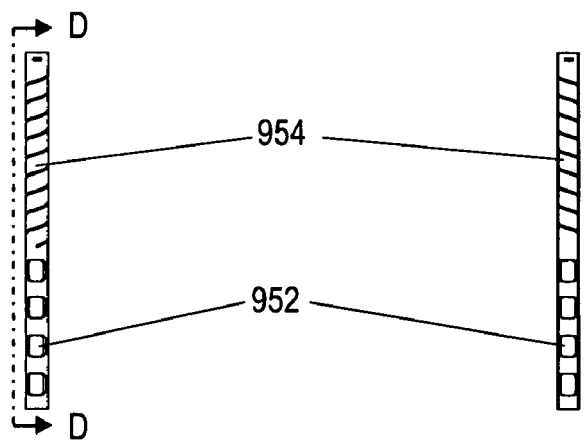

FIGS. 8A-D illustrate a configuration of an outer sleeve 850 suitable for use in a bone fixation device. In the configuration depicted, c-cuts 852 and 852A are used along the length of the sheath 850. The use of c-cuts provides flexibility in the plane perpendicular to the page described along the central axis of the sheath. As depicted, two types of c-cuts can be used, as opposed to a single type of c-cut shown in FIG. 1. At the distal end 804, c-cuts are paired at a location on the length and extend, from opposite sides, toward a central plane of the sheath. The c-cuts enable the teeth of the device, 442 to extend outward, away from the central shaft, into the bone. Toward a proximal end 802, c-cuts are shorter in height and extend across a central plane of the sheath (e.g. a plane in which the guidewire or control rod running through the center of the device would lie). Thus, from one side view, the cuts have an s shape profile, as shown in FIG. 8C. The distal cuts provide flexibility as well as enabling the teeth, 442 to extend through the cuts when the device is actuated. The proximal cuts also provide flexibility, but provide a different degree of flexibility as a result of the orientation and design of the cuts. As depicted in FIG. 8D, which is a cross-section taken along the lines D-D of FIG. 8C, the proximal set of c-cuts give the appearance that the sheath is segmented, while the distal cuts appear as opposing c-cuts. By this method the planar preferential flexibility is established in a representative, but not limiting, embodiment of the device. As will be appreciated by those skilled in the art, more than two-types of c-cuts can be used without departing from the scope of the invention.

FIGS. 9A-D illustrate yet another alternate configuration of an outer sleeve suitable for use in a bone fixation device. In the device depicted, instead of providing the deep c-cuts on the proximal set of cuts depicted in FIG. 8, spiral cuts 954 are provided. The spiral cut provides flexibility in all directions and in all planes. As depicted, c-cuts 952 are used along at least a portion of the length of the sheath 950

Figures 10A, 10B:
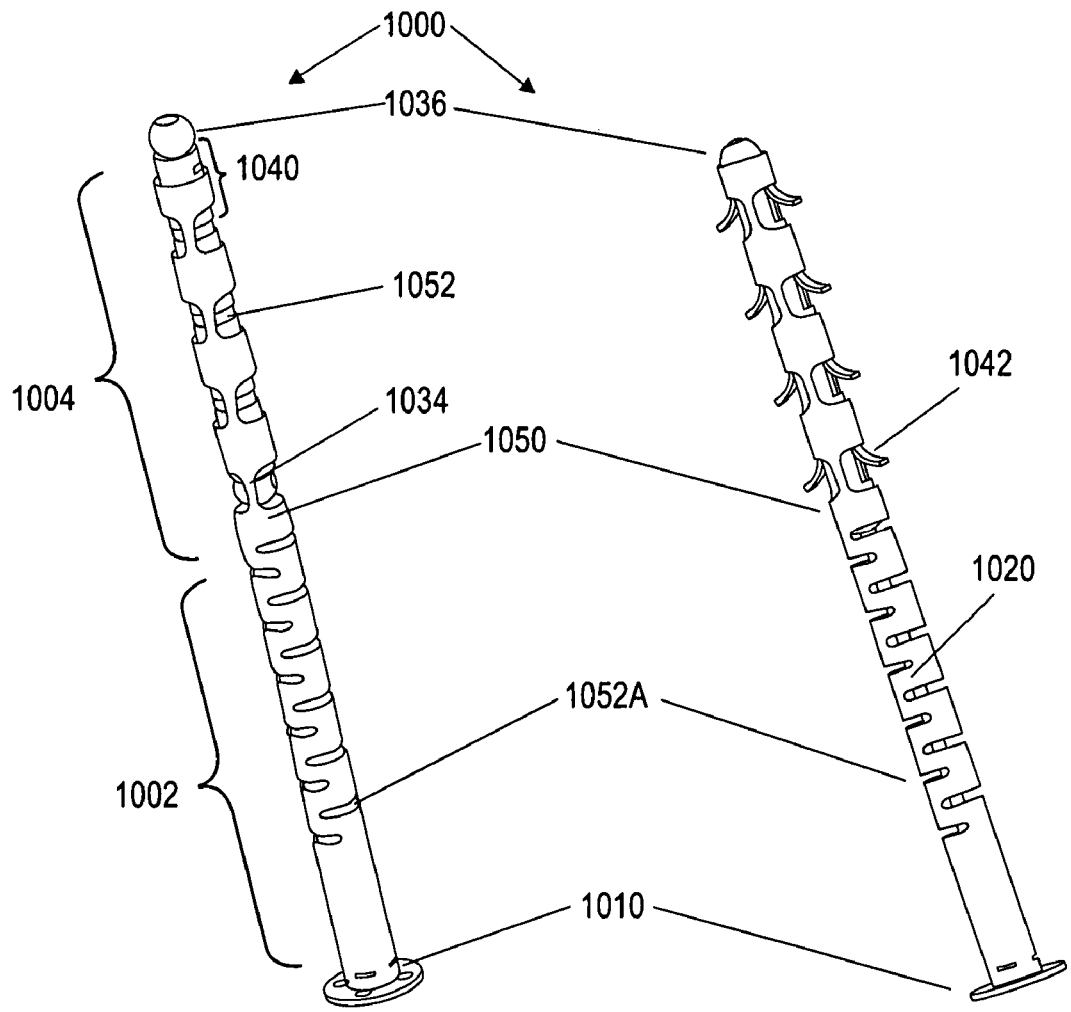
FIGS. 10A-B illustrate another embodiment of an actuable bone fixation device in a pre-deployed and deployed condition.

Turning now to FIGS. 10A-B another embodiment of an actuable bone fixation device 1000 in a pre-deployed and deployed condition is depicted. This embodiment uses an outer sheath 1050 with two types of c-cuts, as illustrated and described with respect to FIG. 8 above. C-cuts 1052 are used along the length of the sheath 1050. As described above, the use of c-cuts provides flexibility in the plane perpendicular to the page along the central axis of the sheath. As with FIG. 8, two types (or more) of c-cuts can be used, as opposed to a single type of c-cut shown in FIG. 1. At the distal end 1004, c-cuts are paired at a location on the length and extend, from opposite sides, toward a central plane of the sheath. The c-cuts enable the teeth of the device, 1042 to extend outward, away from the central shaft, into the bone. Toward a proximal end 1002, c-cuts are shorter in height and extend across a central plane of the sheath (e.g. a plane in which the guidewire or control rod running through the center of the device would lie). Thus, from one side view, the cuts have an s shape profile, as shown in FIG. 10B. The distal cuts provide flexibility as well as enabling the teeth, 1042 to extend through the cuts when the device is actuated. The proximal cuts also provide flexibility, but provide a different degree of flexibility as a result of the orientation and design of the cuts.

Figures 11A, 11B:
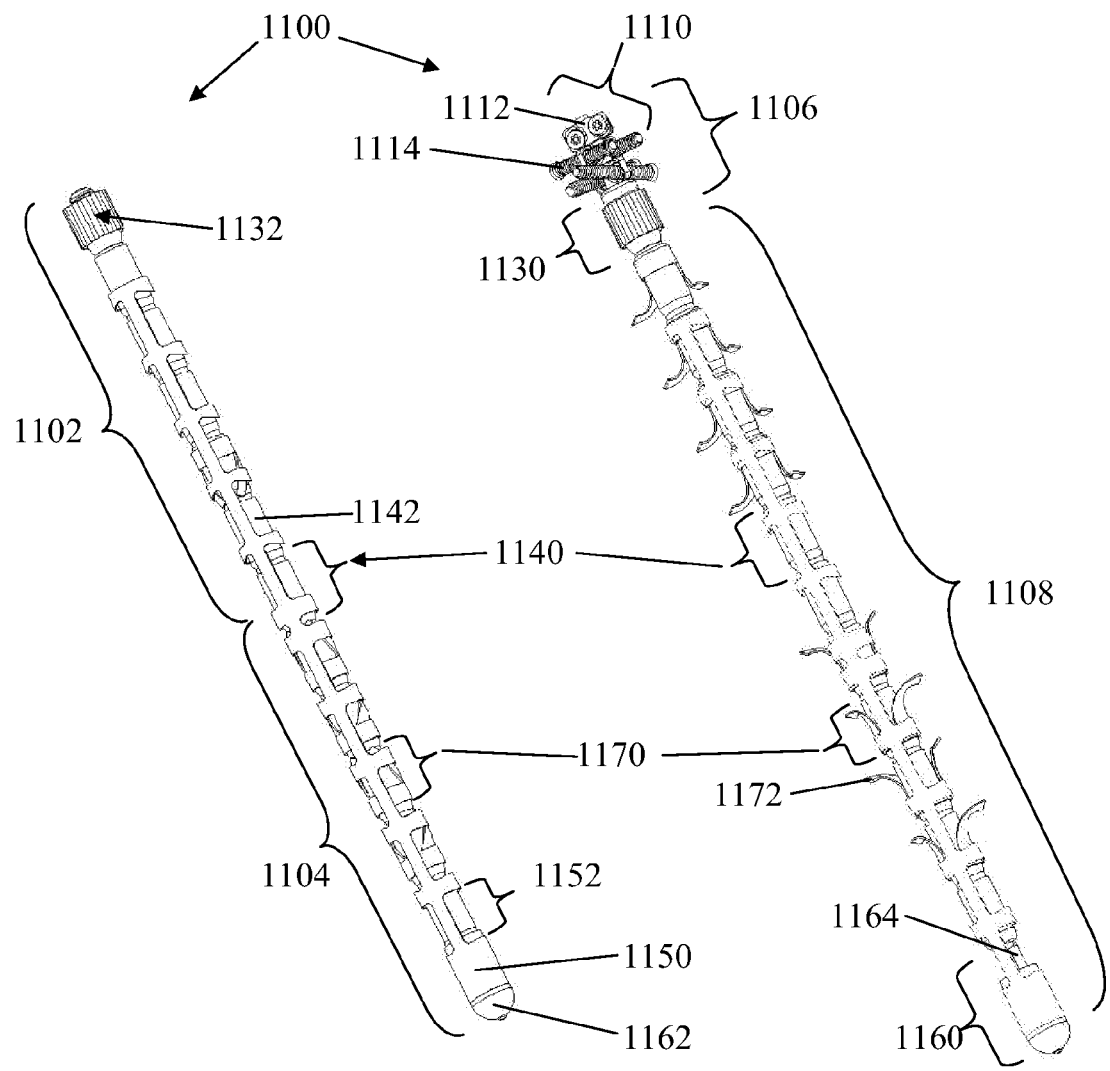
FIGS. 11A-B illustrate yet another embodiment of an actuable bone fixation device in a pre-deployed condition, and deployed condition.

FIGS. 11A-B illustrate another embodiment of an actuable bone fixation device 1100 in a pre-deployed and deployed condition. The device 1100 has a proximal end 1102 and a distal end 1104. Section 1106 is the part of the device that is placed within the metaphyseal section of bone. Section 1106 can also be placed in other types of bone including epiphyseal and diaphyseal. Section 1108 is the section of the device that sits within diaphyseal bone. The proximal end assembly 1110 implements the interface to the metaphyseal bone. Also visible in FIG. 11 are the metaphyseal locking flange 1112 and metaphyseal locking screw 1114. Section 1130 is the universal joint that provides articulation and alignment. Section 1132 is the universal joint sheath. The flexible link 1140 provides flexibility in the lateral medial plane. Section 1142 is the flexible link sheath. Section 1150 is the outer sheath of the device with slot 1152. Section 1160 is the distal end assembly. Section 1162 is the obdurator and Section 1164 is the distal end flexible link male pin. Section 1170 is the diaphyseal anchor with teeth 1172. At the distal end 1104 and the proximal end 1102 the flexible link sections 1140 can be adapted to engage diaphyseal anchoring segments 1170. The anchoring segments 1170, as depicted, fit snugly around the flexible link sections 1130. Each diaphyseal anchoring segment 1170 can have one or more teeth or grippers 1172 that are adapted to enable the teeth to interdigitate within bone when deployed. The teeth 1172 can be configured to enable the teeth to deflect away from the anchoring segment 1170 and into the bone. The teeth 1172 extend at an angle to enable greatest anchoring with the shortest length. As the teeth 1172 dig into the bone, the teeth oppose torque and oppose proximal and rotational movement. The outer sheath 1150 is positioned to maintain the teeth 1172 adjacent the sections of the device until the slots 1152 are adjacent the teeth 1172, at which point the teeth 1172 then can engage the bone. The distal end 1104 can be adapted to form an obdurator 1162 to maintain and/or create the space within the bone through which the device penetrates. As illustrated in FIG. 11B, the teeth 1172 flare away from the device 1100 when adjacent the slots 1152.

Figures 12A, 12B:
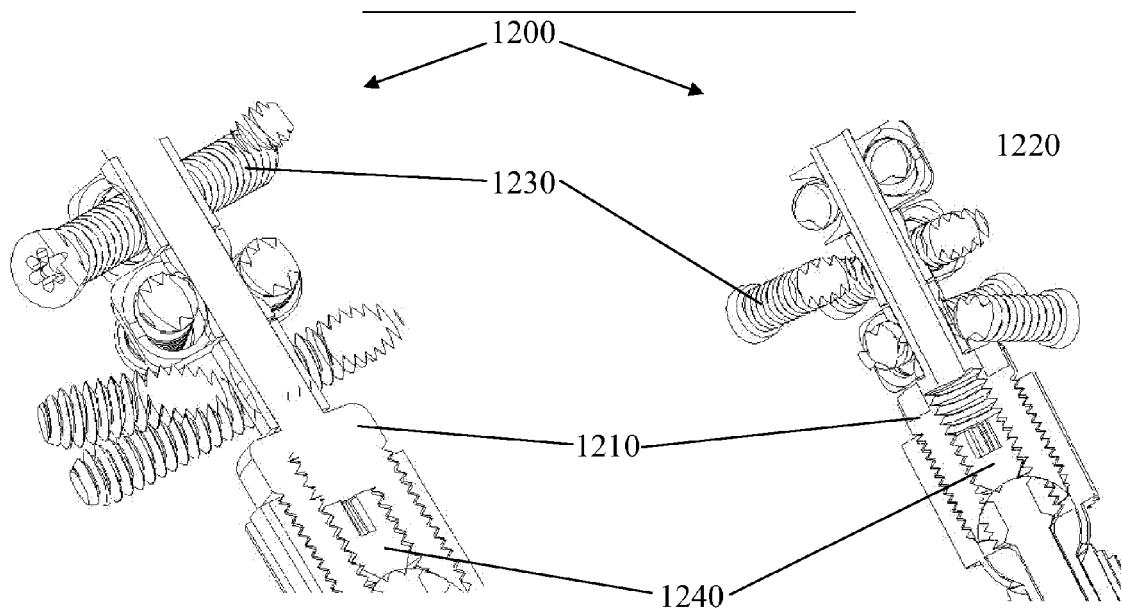
FIGS. 12A-C illustrate the proximal end of an embodiment of an actuable bone fixation device shown in FIG. 11, including component parts.
Figure 12C:
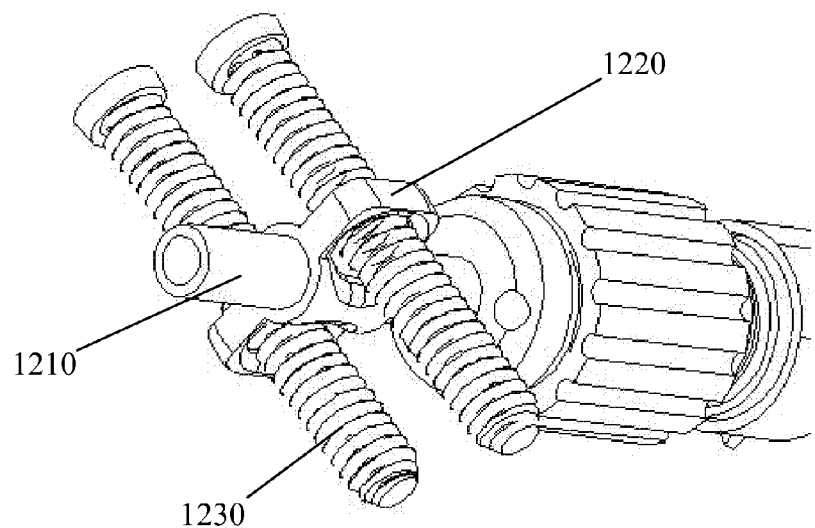

FIGS. 12A-C illustrates an embodiment of the proximal end assembly 1200. This assembly consists of the metaphyseal shaft 1210, one or more metaphyseal locking flanges 1220, the metaphyseal locking screw 1230 and the metaphyseal set screw 1240. The metaphyseal set screw 1900 is depicted in additional detail in FIG. 19. The metaphyseal shaft 1210 translates the fixative forces through the universal joint 1130 to the diaphyseal section 1108. The metaphyseal locking flange 1220 bears on the metaphyseal shaft 1210. The metaphyseal locking screw 1230 threads through the metaphyseal locking flange 1220, cuts into and retains the metaphyseal locking flange 1220 to the metaphyseal shaft 1210, and secures bone, cartilage, animal tissue to the metaphyseal shaft 1210.

Figures 13A, 13B:
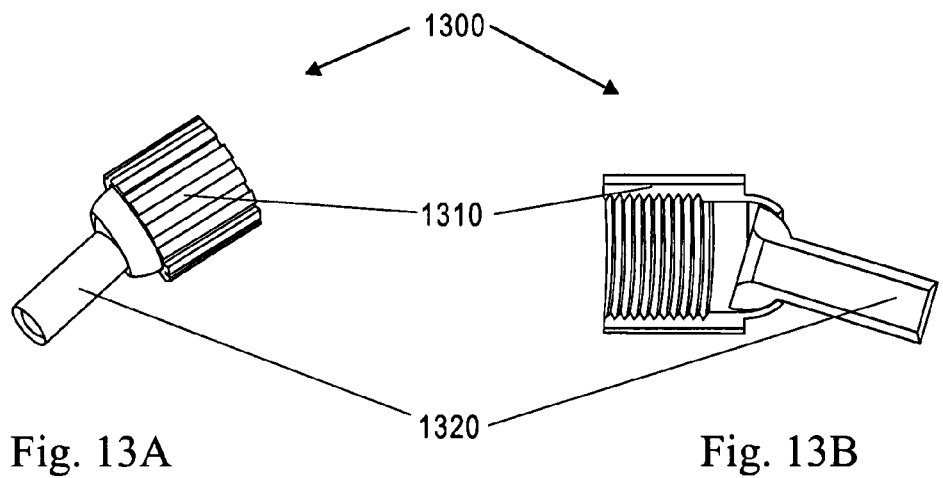
FIG. 13A-B illustrates a universal joint, or u-joint, suitable for use with the devices of the invention.
Figures 20A, 20B:
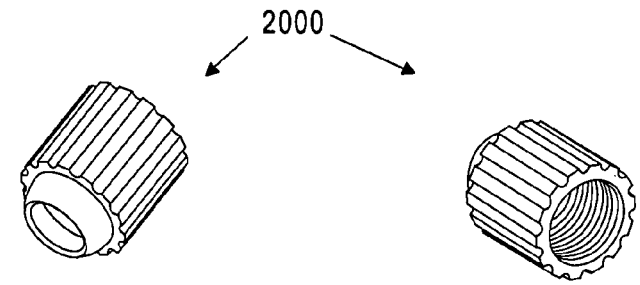
FIGS. 20A-B illustrate an alternative embodiment of a u-joint suitable for use with the devices of the invention.
Figures 21A, 21B:
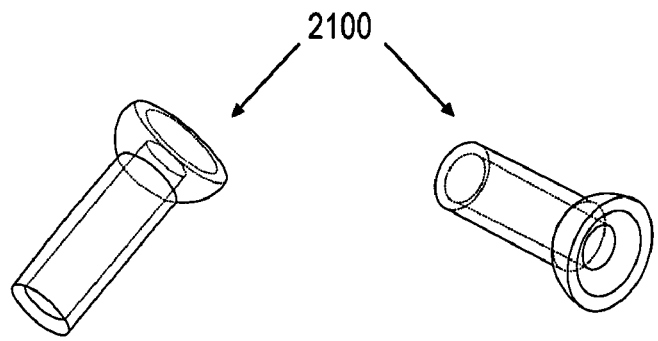
FIGS. 21A-B illustrate an alternative embodiment of a flexible link assembly suitable for use with the invention.

FIGS. 13A-B illustrates an embodiment of a universal joint 1300. This embodiment consists of a sheath 1310, (sheath 2200 is illustrated in additional detail FIG. 20) and a diaphyseal pin 1320, (diaphyseal pin 2100 illustrated in additional detail FIG. 21). The universal joint 1300 allows the metaphysis section 1106 to have hemispherical rotation relative to the axis of the diaphysis section 1108. The diaphyseal pin 1320 connects the universal joint 1300 to the first proximal flexible link 1400.

Figure 14:
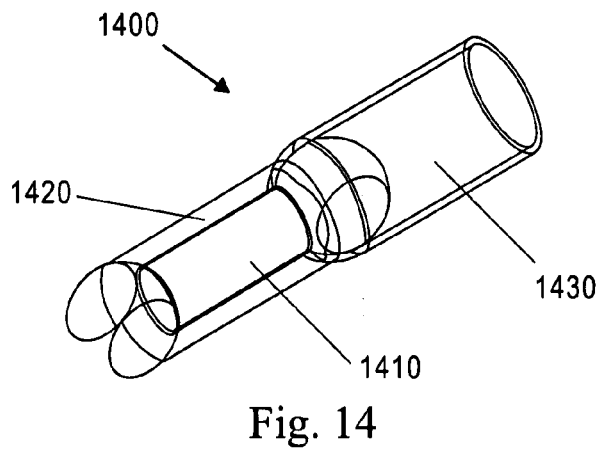
FIG. 14 illustrates a flexible link assembly suitable for use with the devices of the invention.
Figures 22A, 22B:
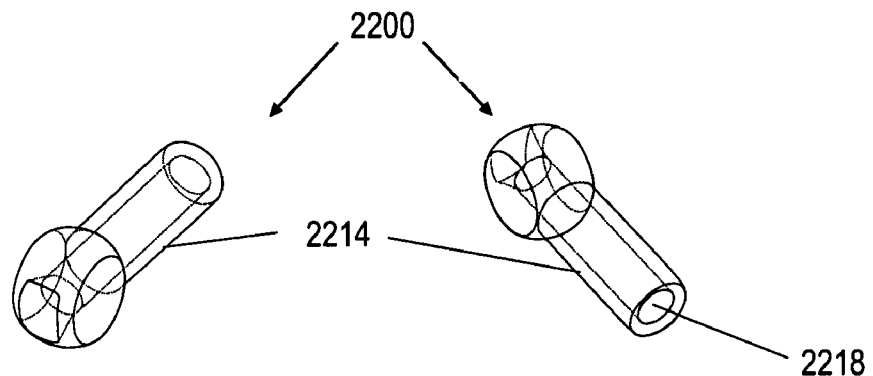
FIGS. 22A-B illustrate a male pin suitable for use with a flexible link assembly.
Figures 23A, 23B:
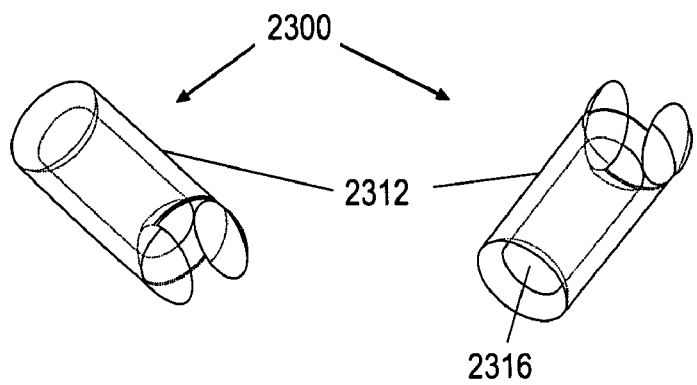
FIGS. 23A-B illustrate an alternative embodiment of a flexible link assembly.
Figures 24A, 24B:
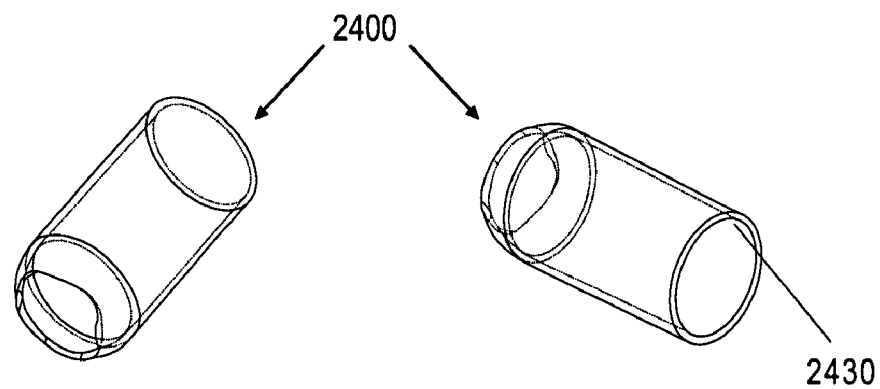
FIGS. 24A-B illustrate a sheath of a flexible link assembly.
Figures 30A, 30B:
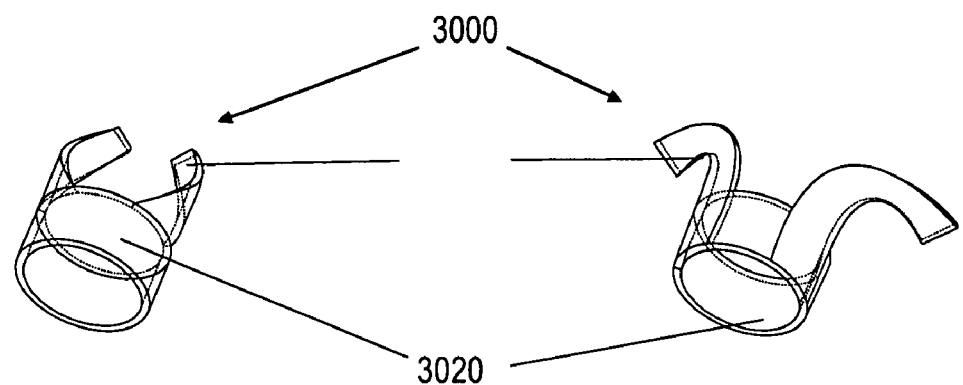
FIGS. 30A-D illustrate a diaphyseal anchor.
Figures 30C, 30D:
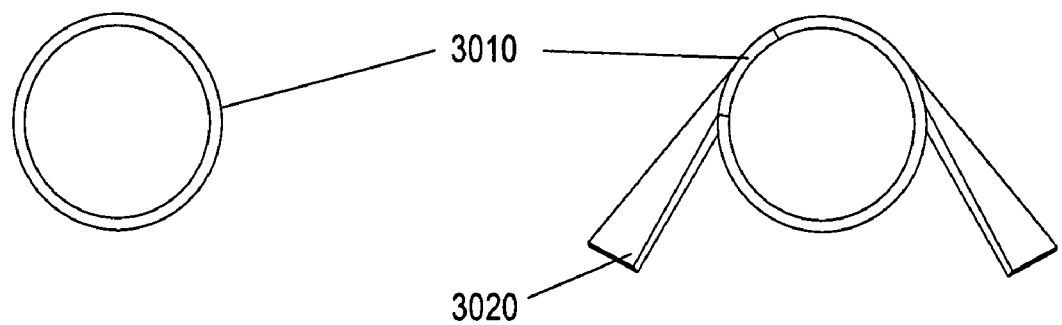

FIG. 14 illustrates an embodiment of the flexible link assembly 1400. The flexible link assembly 1400 is comprised of the female pin 1420, (female pin 2300 is illustrated in additional detail in FIGS. 23A-B), male pin 1410, (male pin 2200 is illustrated in additional detail in FIGS. 22A-B), and the sheath 1430 (sheath 2400 is illustrated in additional detail in FIGS. 24A-B). The male flexible link pin 2200 has bearing surface 2214 that is captured within and slides axially and angularly within the sheath 2400. The female flexible link pin bearing surface 2312 interfaces to the sheath bearing surface 2430. The bores 2218 in the male and 2316 in the female pins accept the flexible link locking pin 2800. The shape of the male flexible link pin 2200 and female flexible link pin 2300 allow medial to lateral flexibility prior to placement of the flexible link locking pin 2800. The bore 2218 through the male flexible link 2200 accepts the flexible link locking pin 2800. Upon insertion and proximal to distal actuation of the flexible link locking pin 2800, the male 2200 and female 2300 flexible link pins are thereby translated such that a locking force is imparted between the sheath 2400 and female flexible link pin. This locking system imparts a resistive force to motion in the medial-lateral plane of the diaphysis and metaphysis. The bore 2218 through the male flexible link pin 2200 is shaped such that there is clearance up to 180 spherical degrees of angulation of the entire assembly, though 30 to 45 degrees of angulation is typical. FIG. 30 show an embodiment of the diaphyseal anchor 3000 which compromise teeth 3010 and an annular section 3020. The diaphyseal anchor slips over and rigidly interferes with the shaft 2400 of the flexible link 1400. The teeth 3010 of the anchoring segment 3000 are designed for specific and maximal fixation to diaphyseal, metaphyseal and epiphyseal bone. The angulation coupled with rotation and shape of the teeth 3010 can take the form of pins, rods, rectangles, frustums of cones, pyramids or other polygons. The number of teeth 3010 is typically two but not limited. In the embodiment shown the teeth 3010 are oriented to prevent axial and rotational translation of the device when deployed within bone. Sets of teeth 3010 can be juxtaposed to resist distal to proximal and proximal to distal axial translation. It is known in the art that the intramedullary space is inconsistent in internal diameter, the diaphyseal anchors 3000 can be specifically designed to accommodate these inconsistencies in internal diameter by changing the shape of the teeth 3010.

Figures 15A, 15B:
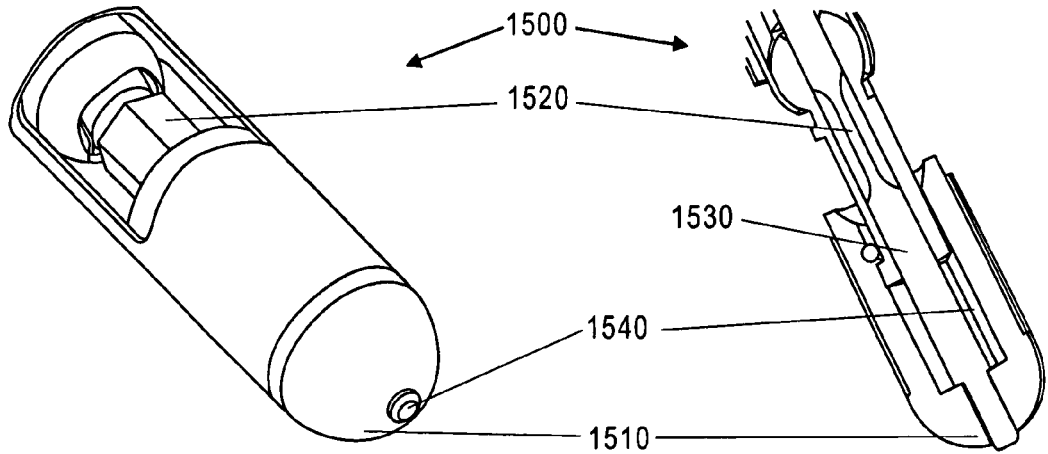
FIGS. 15A-B illustrate a configuration of a distal assembly.
Figures 25A, 25B:
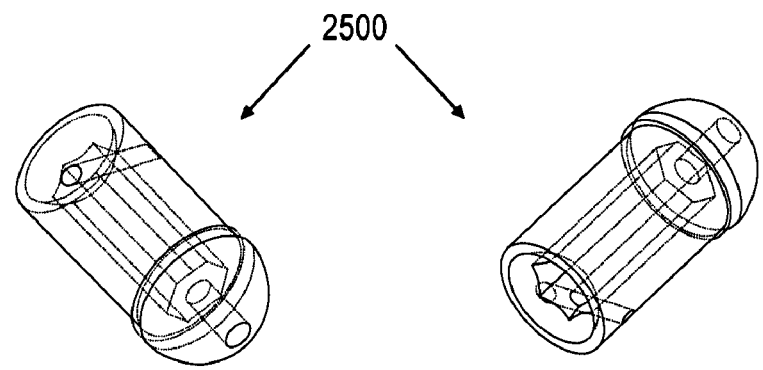
FIGS. 25A-B illustrate an obdurator capture pin.
Figures 26A, 26B:
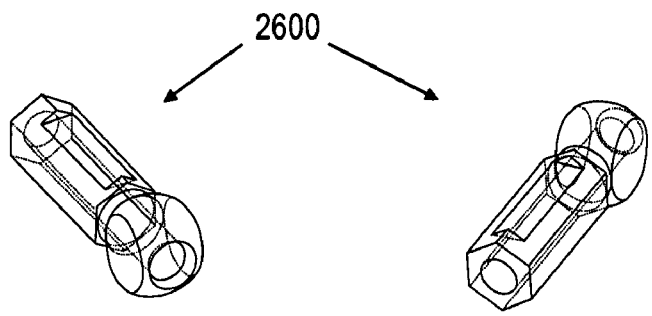
FIGS. 26A-B illustrate a flexible link male pin.
Figure 27:
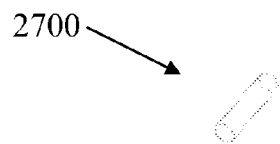
FIG. 27 illustrates a flexible locking pin.
Figures 28A, 28B:
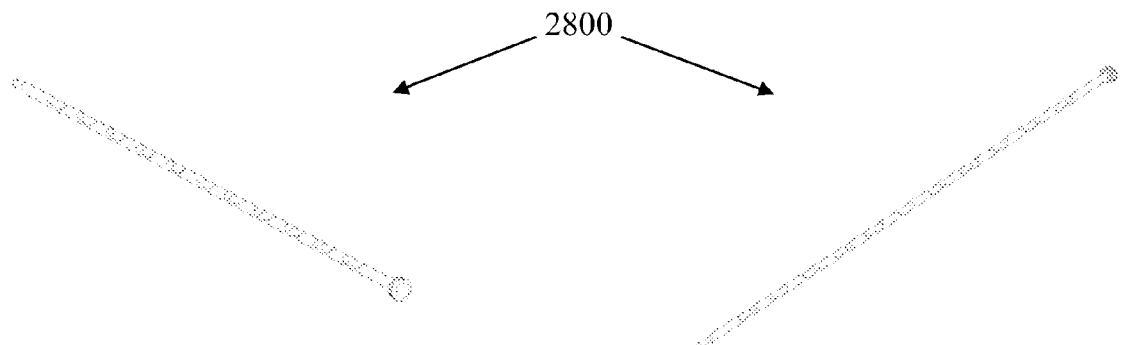
FIGS. 28A-B illustrates a flexible link locking pin.
Figure 29:
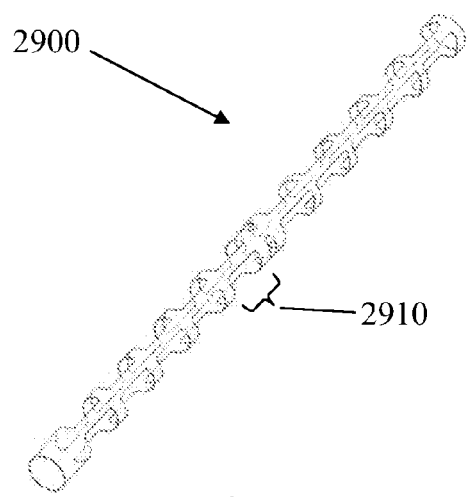
FIG. 29 illustrates an obdurator capture pin.

FIGS. 15A-B illustrate an embodiment of the distal end assembly 1500. The distal end assembly 1500 is comprised of the obdurator or distal bearing surface 1510 (distal bearing surface 2500 is illustrated in additional detail in FIG. 25), distal end flexible link male pin 1520 (flexible link male pin 2600 is illustrated in additional detail in FIG. 26), obdurator captive pin 1530 (obdurator captive pin 2700 is illustrated in additional detail in FIG. 27), flexible link locking pin 1540 (flexible link locking pin 2800 is illustrated in additional detail in FIGS. 28A-B). The distal bearing surface 2500 is connected to the flexible locking pin 2800 and outer sheath 2900 in FIG. 29. The obdurator captive pin 2700 limits the range of movement of the outer sheath 2900 relative to the teeth 3010 of the anchor segments 3000.

Figures 16A, 16B, 16C:
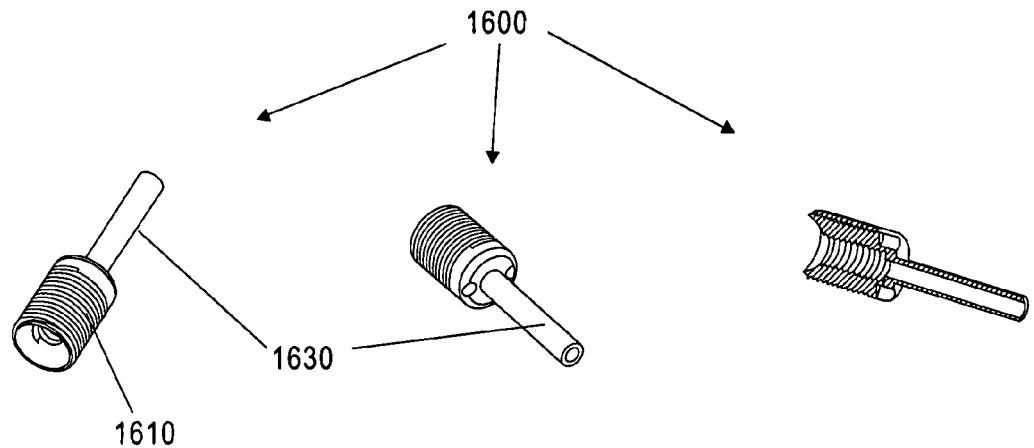
FIGS. 16A-C illustrate a metaphyseal shaft.

FIGS. 16A-C illustrate an embodiment of a metaphyseal shaft 1600. The bearing surface 1630 of this embodiment interfaces to the metaphyseal locking flange 1700, it can be smooth, serrated, knurled, splined, keyed, polygonal or elliptical. The connective surface 1610 connects the metaphyseal shaft 1600 to the universal joint 1300 of FIG. 13. The metaphyseal shaft 1600 provides means to translate fixative forces from the metaphyseal section 1106 of FIG. 11 to the universal joint 1300. Within the metaphyseal shaft 1600 is a means to lock the proximal assembly 1200 of FIG. 12 to the diaphyseal section 1108 of FIG. 11 through the universal joint 1300 and prevent 360 spherical degrees of movement perpendicular and parallel to the longitudinal axis of the diaphysis.

Figures 17, 18, 19:
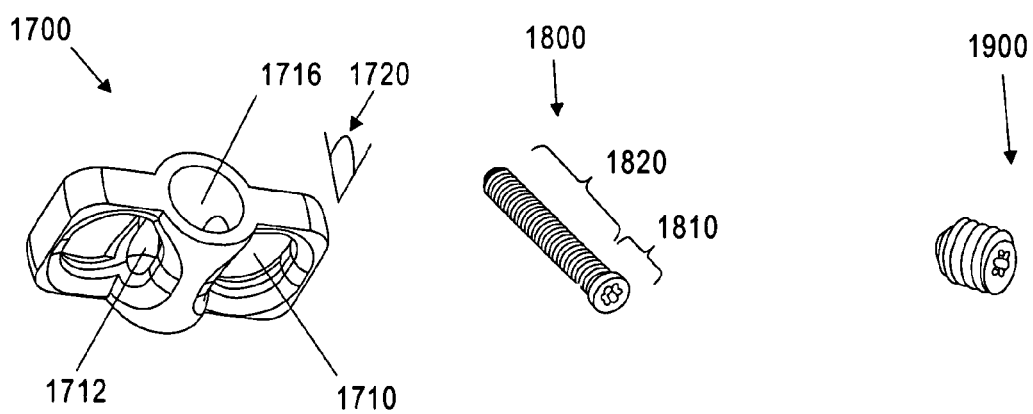
FIG. 17 illustrates a metaphyseal locking flange.
FIG. 18 illustrates a metaphyseal locking screw.
FIG. 19 illustrates a metaphyseal set screw.

FIG. 17 illustrates an alternate embodiment of a metaphyseal locking flange 1700. Screw hole 1710 accepts the metaphyseal locking screw 1800 of FIG. 18. Opening 1716 accepts the metaphyseal shaft 1600 of FIG. 16. Windows 1712 exposes the metaphyseal shaft 1600 and accepts the metaphyseal locking screw threads 1810 and 1820 of FIG. 18 thereby translating forces through metaphyseal locking screw 1800 to metaphyseal shaft 1600 and locking metaphyseal locking flange 1700 to metaphyseal shaft 1600. Opening 1716 allows 360 degree rotation of metaphyseal locking flange 1700 about the metaphyseal shaft 1600. Angle 1720 as described by a line perpendicular to the axis of the shaft and the surface perpendicular to the axis of the screw hole 1710 can be 0 to 180 degrees. This embodiment is meant to be descriptive but not limiting. The function of the metaphyseal locking flange 1700, metaphyseal locking screw 1800 and metaphyseal shaft 1600 allow for translation of the metaphyseal fixation to diaphyseal fixation that is infinitely adjustable in 360 spherical degrees in the axes parallel and perpendicular to the axis of the diaphysis.

FIG. 18 illustrates an embodiment of the metaphyseal locking screw 1800. The threads 1810 and 1820 of the metaphyseal locking screw can be of a single pitch root in diameter or multiple pitch, root and diameters. The threads 1820 and 1810 can take on a variety of features such as smooth, serrated, knurled, splined, keyed, polygonal or elliptical. The metaphyseal locking screw 1800 can be cannulated through its axis to allow deployment by guide wire.

Figures 31A, 31B:
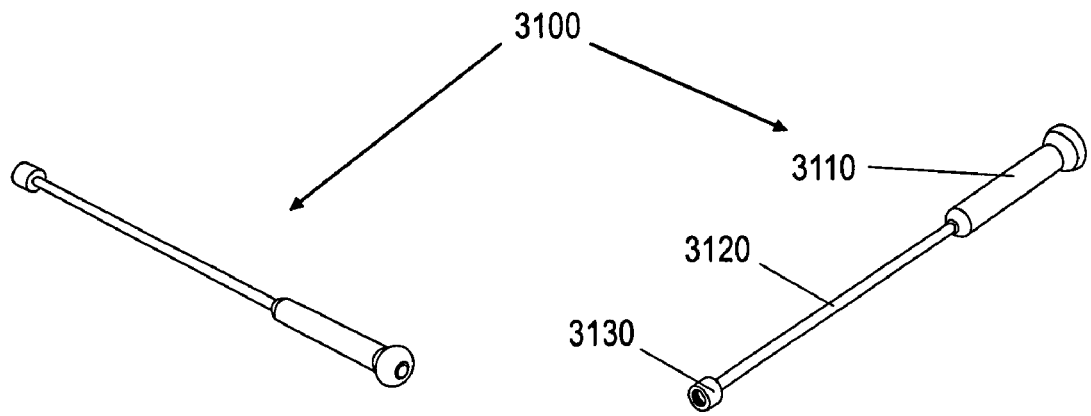
FIGS. 31A-B illustrated a removal tool.

FIG. 31 illustrates an embodiment of a deployment removal tool 3100 for use with the implantable devices of the invention. The tool 3100 consists of a handle 3110, a flexible shaft 3120 and threaded socket 3130.

Figure 32:
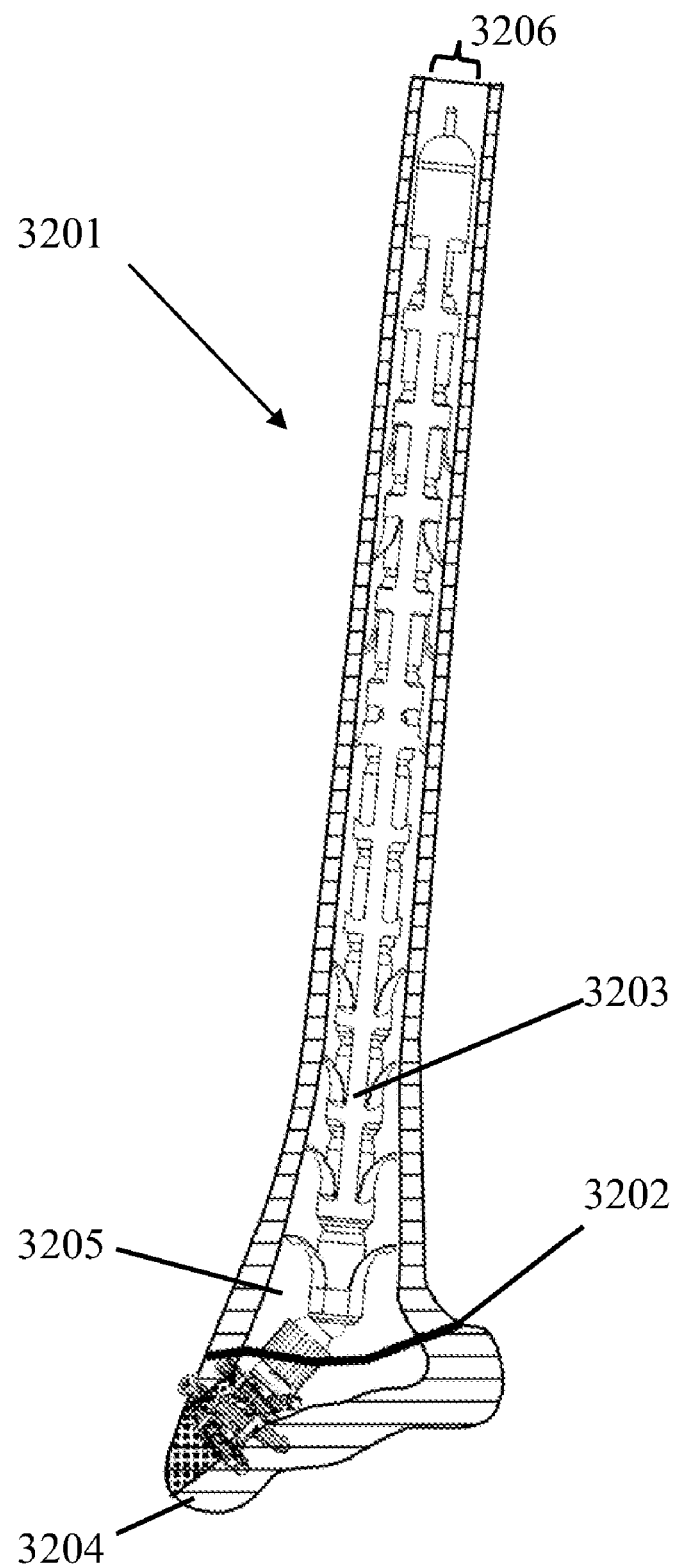
FIG. 32 illustrates a device of the invention deployed in a radius bone.

FIG. 32 illustrate a radius bone 3201 from an arm having a fracture 3202, a radius bone with a device 3203 implanted therein, and a cross-sectional view of a portion of a radius bone with a device implanted therein. While FIG. 32 shows the location of a fracture 3202 in the radius bone 3201, it will be appreciated that the present invention and the various embodiments thereof can be applied to fractures of varying degrees and at any location within a bone structure. Furthermore, it will be appreciated those skilled in the art that the various embodiments of the present invention can be applied to any bone in an animal including human, and the nature of the fracture may be single, compound or fragmented fractures due to external trauma, or due to bone related disease such as osteoporosis. As depicted in FIG. 32, the device 3203, accesses the bone at a bony protuberance 3204 through the trabecular bone. The device 3203 advances through the cortical bone 3205 and, as pictured, is positioned within the intramedullary space 3206 within the bone marrow or other intramedullary constituents.

Figure 33:
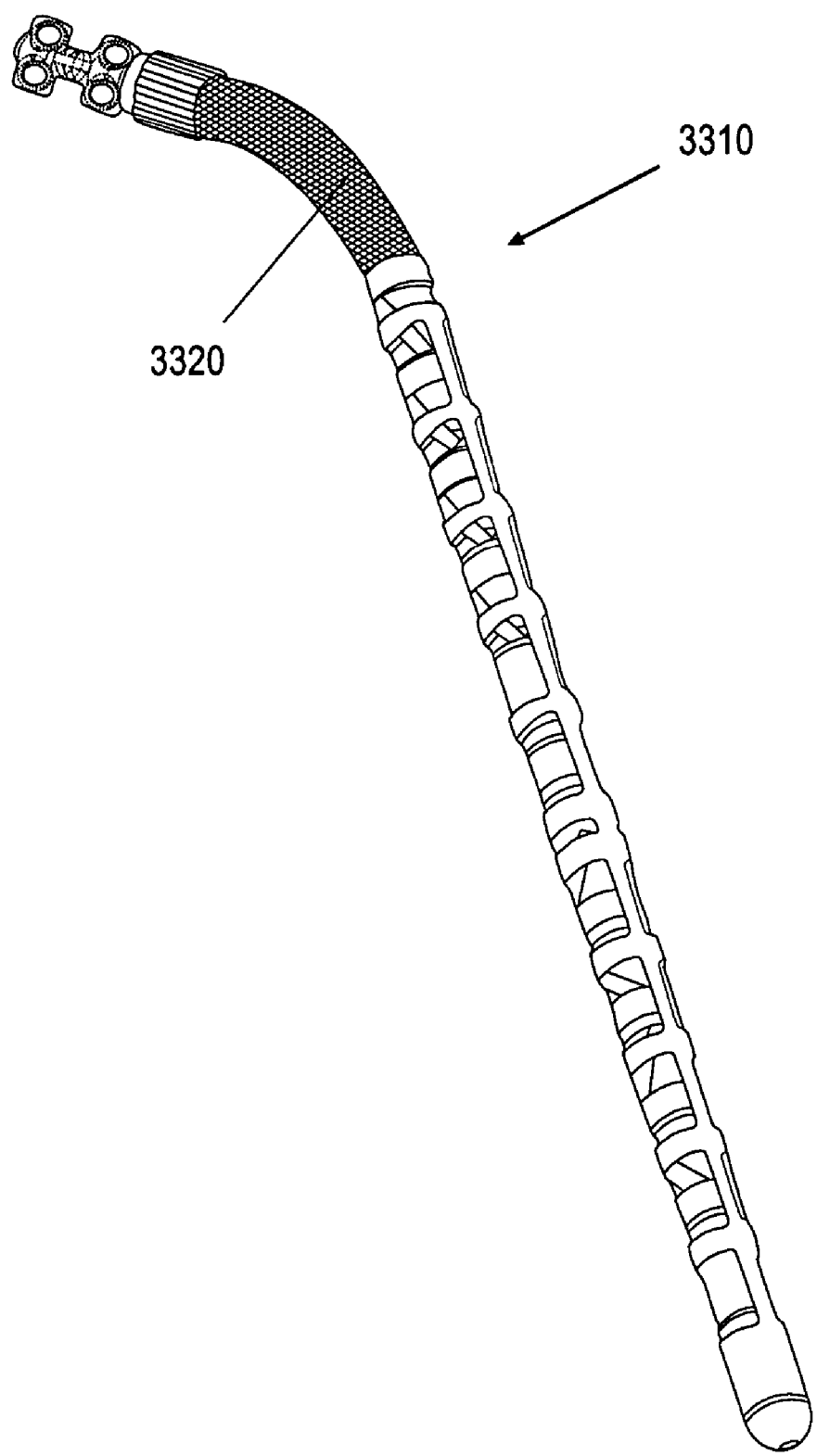
FIG. 33 illustrates another actuable bone fixation device according to the invention.

FIG. 33 illustrates another embodiment of an actuable bone fixation device 3310 having a wire form outer sheath 3320 along at least a portion of the length. The wire sheath can be welded to a stainless steel hypotube, for example, and can be configured to provide the ends be in a turned-out position to prevent rotation.

Figure 34:
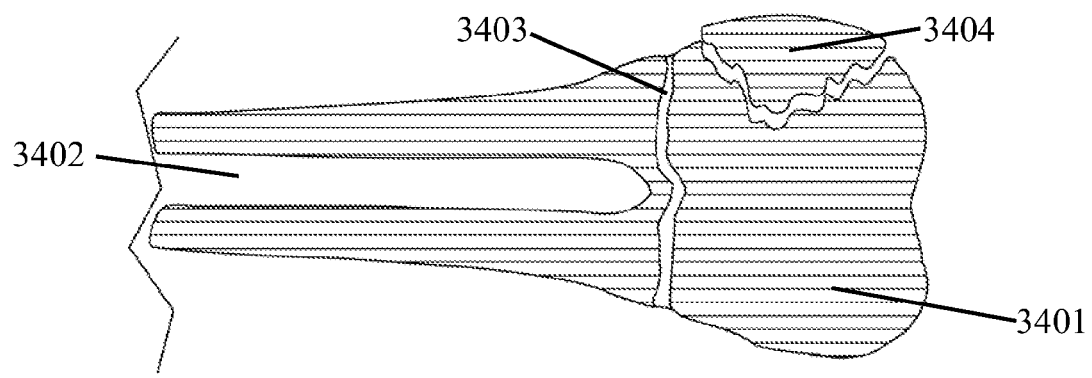
FIG. 34 illustrates a cross-section of a diaphyseal to metaphyseal section in a bone.
Figure 35:
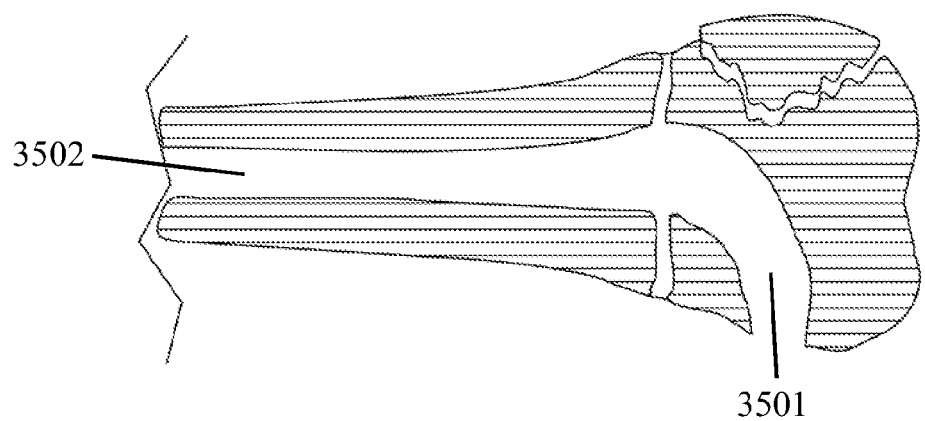
FIG. 35 illustrates a surgical access point into the intramedullary space.
Figure 36:
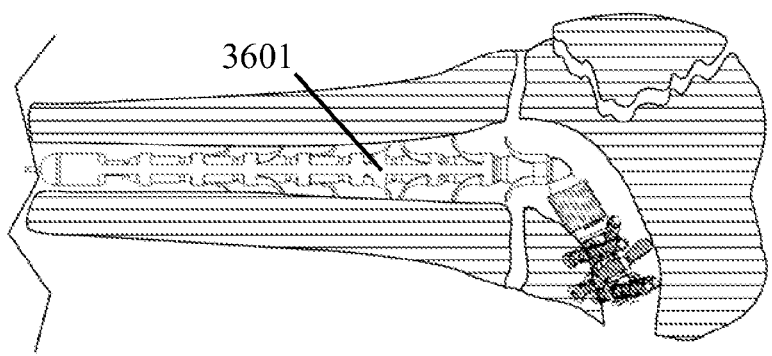
FIG. 36 illustrates a device of the invention positioned within an access lumen.
Figure 42:
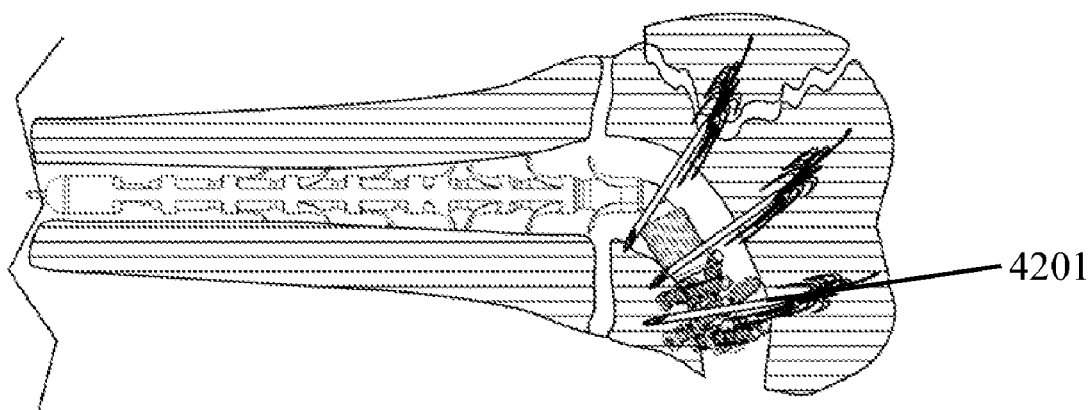
FIG. 42 illustrates a deployed actuable bone fixation device deployed with radially positioned barb-screws.
Figure 43:
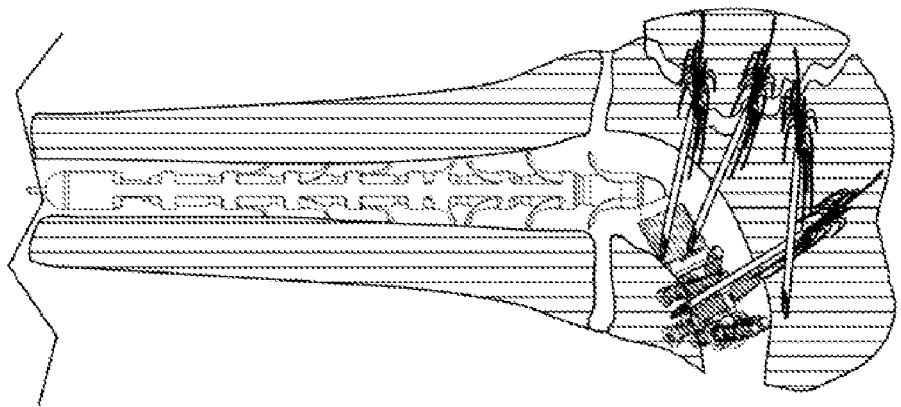
FIG. 43 illustrates a deployed actuable bone fixation device deployed with mixed orientation barb-screws.

A challenge in bone fixation across the diaphysis to the metaphysis has been securing the cancellous bone in the metaphysis. This bone is sponge-like and can be brittle or vacuous, particularly in osteoporotic patients. A physician must choose between rigid to rigid surface fixation and rigid to porous surface fixation. One embodiment of a system capable of achieving rigid to porous fixation in skeletal bone is described here. FIG. 34 is a cross section of a diaphysis to metaphysis transition of one of the skeletal bones of an animal or human. A cancellous or porous bone 3401 of the metaphysis is depicted. An intramedullary space 3402 is depicted along an axis of the bone. FIG. 34 illustrates a portion of a bone 3403 having a transverse fracture and an oblique fracture bone chip 3404. The challenge in practice is to tie these three bone fragments, one of the diaphysis and the two of the metaphysis together. Embodiments of this invention enable the formation of a foundation rigidly secured in all Cartesian, polar, spherical and cylindrical axes of the diaphysis. FIG. 35 demonstrates surgical access to the intramedullary space 3502 after creating a lumen 3501 from the metaphyseal bone to the diaphyseal bone. The device, 3601, described in the preceding invention description is placed in the lumen and deployed as shown in FIG. 36. FIG. 37 illustrates a novel barb-screw. The barb-screw consist of a tool interface such as a hex head, flat head, torx head, or Phillips head screw drive Feature 3701. Feature 3702 is a thread that threads into and locks to the metaphyseal section of the device 3601 or through the metaphyseal locking flange 1700. The barb screw is comprised of wires or filaments, 3703, of nickel titanium or other rigid metallic, polymer, or ceramic material capable of deformation over a significant strain without yield or fracture. In one embodiment, the wires or filaments are beveled at the end 3704, to create a sharp or penetrating end. Upon removal of suppressive force such as a sheath 3705 or actuation by thermal, electrical, or mechanical means, the filaments undergo a physical change and change shape to 3801 or other shape, as shown in FIG. 38. A plurality of wires or filaments 3901 may be positioned along the length of the barb-screw as shown in FIG. 39. The wires or filaments may serve multiple purposes, such as creating a thread to facilitate placement of the barb screw. Upon removal of the restraining force or application of an external motive force the dual purpose screw feature, 4001, can then turn and arc to capture bone as shown in FIG. 40. The barb-screw can be deployed through the device 3601, retained by the thread, 4001, to the device 3601, and capture bone transverse 4101 to the placement of the device 3601 as shown in FIG. 41. The barb-screw can capture bone radially, 4201, from the device 3601 as shown in FIG. 42. A mixed mode of bone fragment capture may be utilized as well as shown in FIG. 43.

The actuable barb screw is adapted to provide a small diameter with great amount of surface area upon deployment; a combination of screw and barb capture modalities; locking threads to the device 3601; and an activation by removal of external force or by imparting energy to the device by thermal, electrical, optical, or mechanical means. Any frequency of the spectrum of electromechanical radiation may be used to impart such energy to the system.

As will be appreciated by those skilled in the art, the actuable barb screw can be configured to provide superior holding force and capture by employing rigid materials that change their radius of capture area after undergoing a change. Further, the barbs may be configured to be displaced as threads to aid insertion of the barb-screw.

Figure 44:
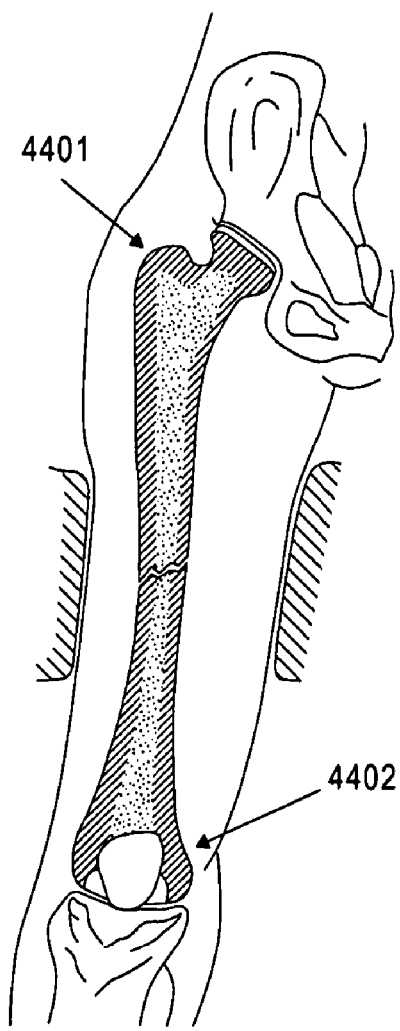
FIG. 44 illustrates a femur of a patient with an indication of access points.

Additional embodiments, methods, and uses are envisioned in accordance with the inventive attributes. Thus, for example, the drill can be used to bore an access opening into the trabecular (cancellous) bone at a bony protrusion located at a proximal 4401 or distal 4402 end of FIG. 44 of a bone having a fracture; where the proximal end in the anatomical context is the end closest to the body midline and the distal end in the anatomical context is the end further from the body midline. For example, on the humerus, at the head of the humerus (located proximal, or nearest the midline of the body) or at the lateral or medial epicondyle (located distal, or furthest away from the midline); on the radius, at the head of the radius (proximal) or the radial styloid process (distal); on the ulna, at the head of the ulna (proximal) or the ulnar styloid process (distal); for the femur, at the greater trochanter (proximal) or the lateral epicondyle or medial epicondyle (distal); for the tibia, at the medial condyle (proximal) or the medial malleolus (distal); for the fibula, at the neck of the fibula (proximal) or the lateral malleoulus (distal); the ribs; the clavicle; the phalanges; the bones of the metacarpus; the bones of the carpus; the bones of the metatarsus; the bones of the tarsus; the sternum and other bones with adequate internal dimension to accommodate mechanical fixation. As will be appreciated by those skilled in the art, access locations other than the ones described herein may also be suitable depending upon the location and nature of the fracture and the repair to be achieved. Additionally, the devices taught herein are not limited to use on the long bones listed above, but can also be used in other areas of the body as well, without departing from the scope of the invention. It is within the scope of the invention to adapt the device for use in flat bones as well as long bones.

Figure 45:
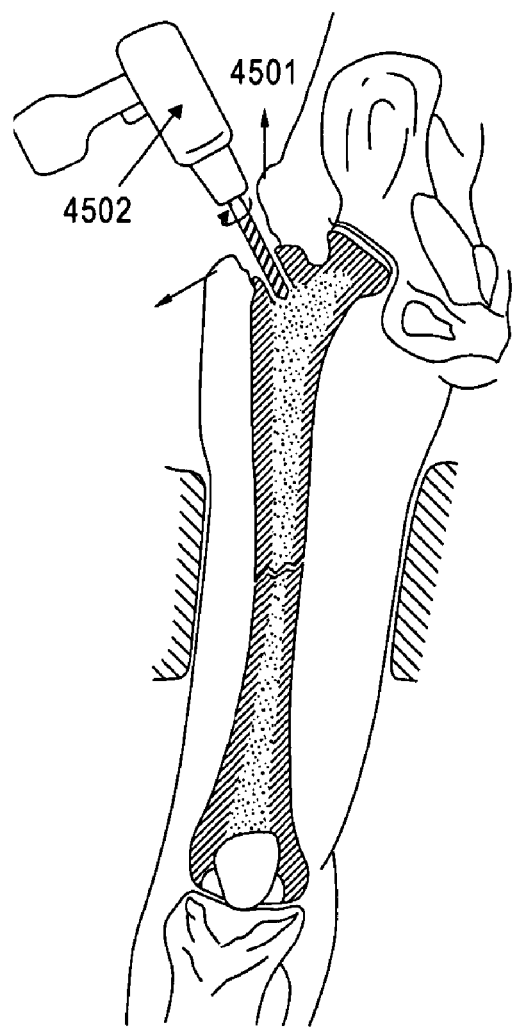
FIG. 45 illustrates a femur of a patient with a drill accessing the shaft.

In accordance with one embodiment of the method, an incision 4501 as shown in FIG. 45 may be made on the skin of the patient at a location substantially aligned with, for example, a proximal or distal end of the fractured bone (e.g., an end of the bone where cancellous bone is located). The incision thus allows the skin substantially surrounding the incision at location to be pulled or folded back in order to expose the end of the fractured bone. The location of the access site is chosen by the surgeon based upon the diagnosis of the best entry point for the various devices of the invention. Access points include-areas of the bone that are considered minimally invasive. These sites include the areas of the bones at the intersection at the elbow, knee, and ankle, i.e. the trabecular or cancellous bone located at the end of the long bones.

A drill bit may be operated 4502 by the surgeon to bore an opening to create a space within a central portion of the fractured bone. See, U.S. Pat. No. 6,699,253 to McDowell et al. for Self-Centering Bone Drill. Although, as will be appreciated by those skilled in the art, any tool capable of boring through the layer of tissue and into the fractured bone may be used without departing from the scope of the invention. One example of such a device includes, but is not limited to, a coring reamer 4601 as shown in FIG. 46 which may be used to bore into the bone as discussed below. See, U.S. Pat. No. 6,162,226 to de Carlo Jr. for Long Bone Reamer with Depth Stop Indicator. The coring reamer in one embodiment may be configured to harvest a bone plug from the access point for future closure of the surgically created wound. This method would facilitate healing, and improve the surgical outcome in regards to strength, infection, and immune rejection of any foreign body.

The drill or reamer can be operated along the length of the bone in order to reach the location of the bone fracture. As would be appreciated by those skilled in the art, the use of a flexible reamer may require distal guidance 4602 to prevent inadvertent injury or damage to the surrounding bone. In order to provide such guidance, a wire, or other thin resilient, flexible entity of minimal cross sectional size, can be provided to provide such guidance. The guide wire is placed subsequent to creation of the access site and exposure of the space. A secondary access hole 4603 can be created distal to the initial access. The guide wire is then deployed using standard technique into the bone space, across the bone from the proximal access hole to the secondary access hole. Further, the device can use its distal end as an obdurator to create a path through the bone, through the intramedullary space, and/or across a fracture, is desired.

A centering entity 4604, may be used to "float" the guide wire away from the extremities of the inside feature of the space and bone. The guide wire and centering entity may be left in place throughout the procedure and may be present considerable advantages for subsequent cleaning, and placement of the reinforcement device. The second distal access may be optional. The centering entity, or visualization under fluoroscopy, may obviate the need for the distal access. In this embodiment of the use of the guide wire, the centering entity can be used independently of the distal access. Another embodiment eliminates both the distal access and the centering device. In that embodiment, only the guide wire is used to center the reaming tool. In another embodiment the guide wire is not used. The reaming tool is centered by technique of visualization under fluoroscopy or other means.

Thereafter, a channel within the bone, such as within the intramedullary space, is created and is cleaned to remove the bone and fat debris prior to the deployment of the reinforcement device through the space within the fractured bone. Irrigation and cleaning of the channel created in the bone would be accomplished using techniques known in the art. For example, irrigation can be accomplished using water, saline or ringers solution. Solutions that include other solutes may also be beneficial; for example, solutions of having functional or therapeutic advantage, as well as growth stimulation and anti-infection agents such as antibiotic, including gentomiacin.

A lavage system can also be used, such as a lavage system 4701 shown in FIG. 47 which includes bi-directional flow path tubing. The lavage system can be used to remove bone fragments and fat debris from space as a result of using the drill or coring reamer. In one embodiment, the lavage system includes an inflow of saline solution provided into the space of the fractured bone, while a vacuum suction by the flow path tuning removes the bone and debris fragments loosened in saline solution. In this manner, the space within the fractured bone may be cleaned and prepared for the deployment of the reinforcement device to the fracture site of the bone. See, U.S. Pat. No. 4,294,251 to Greenwald et al. for Method of Suction Lavage.

The coring reamer or drill can be used to create a space within the fractured bone, as well as past the location of the fracture itself The lavage system can be similarly configured to clean the debris within the space including at the location of the fracture. The reamer or drill may traverse the fracture site independently or in conjunction with a protective sheath across the fracture site. As will be appreciated by those skilled in the art, the space may be reamed from both ends, from a proximal opening and a distal opening up to the fracture site.

As discussed above, in accordance with one embodiment of the present invention, the physical trauma to the patient is substantially minimized in treating the bone fracture by limiting the incision to a relatively small location corresponding to the proximal end of the fractured bone, allowing faster patient recovery and wound healing.

This procedure can use a smaller opening than the procedure used for an intramedullary nail. Further, the device and its operation, minimizes or eliminates the risk of pain or necrosis of the bone.

Candidate materials for the devices and components would be known by persons skilled in the art and include, for example, suitable biocompatible materials such as metals (e.g. stainless steel, shape memory alloys, such a nickel titanium alloy nitinol) and engineering plastics (e.g. polycarbonate). See, for example U.S. Pat. No. 5,190,546 to Jervis for Medical Devices Incorporating SIM Memory Alloy Elements and U.S. Pat. No. 5,964,770 to Flomenblit for High Strength Medical Devices of Shape Memory Alloy. In one embodiment, the outer exoskeleton or sheath may be made of materials such as titanium, cobalt chrome stainless steel. Alternatively, the sheath can be made of biocompatible polymers such as polyetheretherketone (PEEK), polyarylamide, polyethylene, and polysulphone.

As will be appreciated by those skilled in the art, the polymer or thermoplastic used to make any of the components of the device, such can comprise virtually any non-radiopaque polymer well known to those skilled in the art including, but not limited to, polyether-etherketone (PEEK), polyphenylsolfone (Radel®), or polyetherimide resin (Ultem®). If desired, the polymer may also comprise a translucent or transparent material, or a combination of materials where a first material has a first radiopacity and the second material has a second radiopacity. Suitable PEEK can include an unfilled PEEK approved for medical implantation. The devices and components can be formed by extrusion, injection, compression molding and/or machining techniques, as would be appreciated by those skilled in the art.

Other polymers that may be suitable for use in some embodiments, for example other grades of PEEK, such as 30% glass-filled or 30% carbon filled, provided such materials are cleared for use in implantable devices by the FDA, or other regulatory body. The use of glass filled PEEK would be desirable where there was a need to reduce the expansion rate and increase the flexural modulus of PEEK for the instrument. Glass-filled PEEK is known to be ideal for improved strength, stiffness, or stability while carbon filled PEEK is known to enhance the compressive strength and stiffness of PEEK and lower its expansion rate. Still other suitable biocompatible thermoplastic or thermoplastic polycondensate materials may be suitable, including materials that have good memory, are flexible, and/or deflectable have very low moisture absorption, and good wear and/or abrasion resistance, can be used without departing from the scope of the invention. These include polyetherketoneketone (PEKK), polyetherketone (PEK), polyetherketoneetherketoneketone (PEKEKK), and polyetheretherketoneketone (PEEKK), and generally a polyaryletheretherketone. Further other polyketones can be used as well as other thermoplastics. Reference to appropriate polymers that can be used in the tools or tool components can be made to the following documents, all of which are incorporated herein by reference. These documents include: PCT Publication WO 02/02158 A1, to Victrex Manufacturing Ltd. entitled Bio-Compatible Polymeric Materials; PCT Publication WO 02/00275 A1, to Victrex Manufacturing Ltd. entitled Bio-Compatible Polymeric Materials; and PCT Publication WO 02/00270 A1, to Victrex Manufacturing Ltd. entitled Bio-Compatible Polymeric Materials. Still other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used as well for portions of the instrument that are desired to be radiolucent.

Moreover, the outer exoskeleton structure, or sheath, may be a hybrid of metal components to accommodate the interdigitation features or die tubular part of the exoskeleton.

In still other embodiments, the device or components can be coated with therapeutic agents or can be configured from polymers with therapeutic agents incorporated therein.

The device may be of a variety of lengths and diameters. The length and diameter of the device may be determined by the fracture site and patient anatomy and physiology considerations. The length must traverse the fracture across its angularity to the internal diameter. The diameter ranges from the minimum to the maximum internal diameter for the space. Though not restricted to these values, the length may vary from 1000 mm to 1 mm and the diameter may range from 0.1 mm to 100 mm. These interdigitation features are designed to penetrate 25 to 75% of the cortical bone at the site of the fracture. The designs of the device allow for a multiple lengths of interdigitation in different devices and within the same device.

Figure 49:
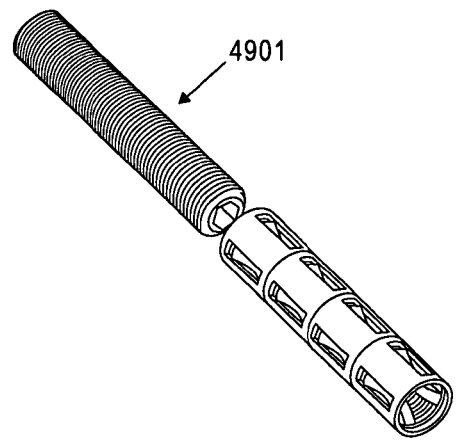
FIG. 49 illustrates the device of FIG. 48 from a perspective view.

The interdigitation features, upon full deployment, may be configured to open out and into the surrounding bone to hold in place the fragments of the fractured bone. This can be achieved with the use of an inner sleeve 4901 as shown in FIG. 49. In one embodiment of the present invention, the cross bone fracture stabilization assembly may be removed after a predetermined period of time during which the bone at the fractured site has substantially and completely healed. The inner sleeve 4801 as shown in FIG. 48 is then removed and the guide wire 4802 may be used to remove the cross bone fracture stabilization assembly 4803 in one embodiment. Alternatively, within the scope of the present invention, the cross bone fracture stabilization assembly may be permanently positioned within the space so as to remain integrally intact with the bone tissues substantially at the fractured site.

Figure 50:
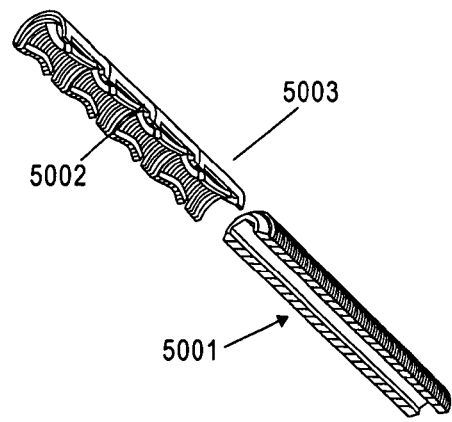
FIG. 50 illustrates a cross-sectional view of the device of FIG. 48.

As will be appreciated by those skilled in the art, the device can be configured such that an outer sleeve is removable upon deployment of the interdigitation feature (e.g. expansion of the teeth away from the central axis). In another embodiment, the inner sleeve 5001 as shown in FIG. 50 can be removed causing the teeth 5002 to collapse inward toward the central axis of the outer exoskeleton or sheath 5003. In an embodiment according to this design, the device to bone connective force would be eliminated upon removal of the inner sleeve. The teeth of exoskeleton or sheath either retract back towards the central axis of the device or upon pulling the device towards the proximal opening in the bone, the teeth disengage from the bone. This allows facile removal of the device. In one embodiment, the outer exoskeleton or sheath may be removed by applying a force opposite in direction away from the outer exoskeleton.

Figure 51:
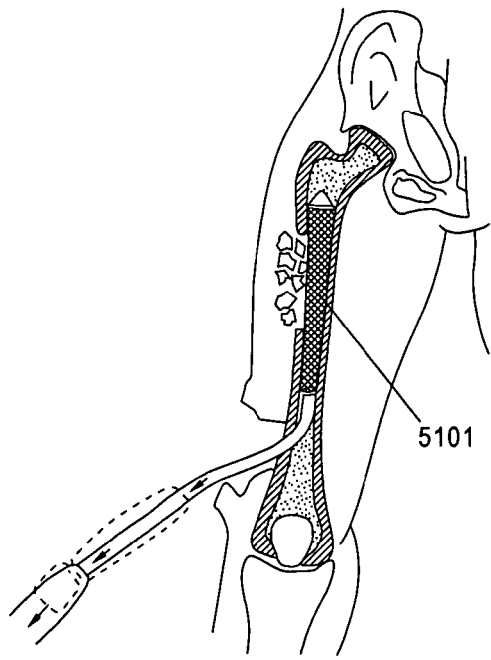
FIG. 51 illustrates deployment of a cross-bone stabilization device.

While the description above relates to cross bone deployment, this stabilization device is suitable to communicate anatomical forces across any areas of weakened bone. The location of the weakened bone is identified by suitable diagnosis. The cross bone stabilization device 5101 as shown in FIG. 51 within the scope of the present invention may be deployed across the region of weakened bone. Within the scope of the present invention, the cross bone stabilization device may be made from large diameter for long bones or very small sizes for bones of the hand or foot. The diameter and length of the device are designed for fixation of the bone internally.

Figure 52:
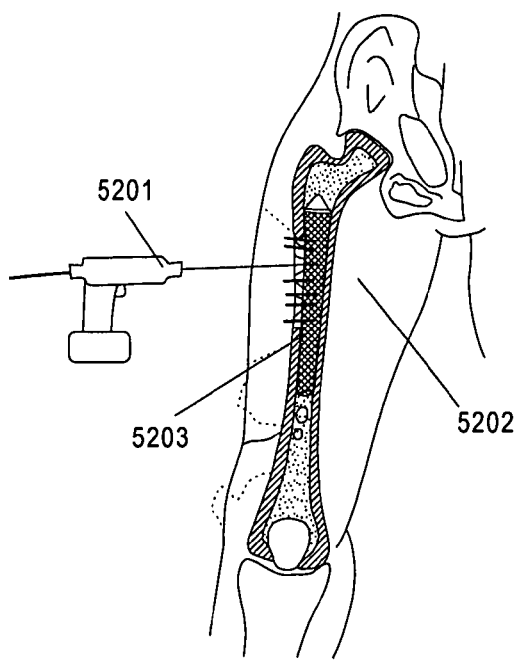
FIG. 52 illustrates positioning of a reinforcement device at a desired location.

After positioning the reinforcement device at the desired location within the space so as to substantially be in contact, with the bone fracture, using a K-wire driver 5201 as shown in FIG. 52, the bone fragments are attached to the reinforcement device 5202 that is fully deployed, properly positioned within the space and structurally expanded to substantially fill the space where it is positioned. K-wires 5203, i.e., thin, rigid wires, can be used to stabilize bone fragments. These wires can be drilled through the bone to hold the fragments in place. As would be appreciated by those skilled in the art, the k-wires can also be placed percutaneously (through the skin).

More specifically, upon complete removal of the introducer described above from the central aperture, the bone fragments can be attached to the device by K-wires deployed using a K-wire driver so that the fragments are substantially and properly aligned with the bone structure guided by the reinforcement device during the recuperation process. Furthermore, optionally, bone cement, allographic bone, harvested bone, cadaver bone or other suitable bony matrices maybe introduced into the space after removing the introducer to substantially fill the space from the incision site to the reinforcement device. Moreover, prior to closing the incision site, a bone plug may be deployed at the opening of the space of the bone to substantially seal the bony matrix and/or to seal the space.

After the device has been implanted according to any of the techniques described herein, the incision site is closed with stitches, for example, to allow the fracture, and the fragments to heal.

In another embodiment of the device includes a plurality of independent structural members with inner or outer position across weakened or fractured bone. Though each independent structural member is placed uniquely in bone additional wires, threads, sutures may tie these together across bone so that the plurality of structural members are linked and form a rigid construction that resists anatomical and typical patient loading and forces. In FIG. 53 are shown examples 5301, 5302, 5303 and 5304 of independent structural members connected by high tensile strength connective members. With this construction, very small reinforcement and fixation devices may be constructed in situ.

Figure 54:
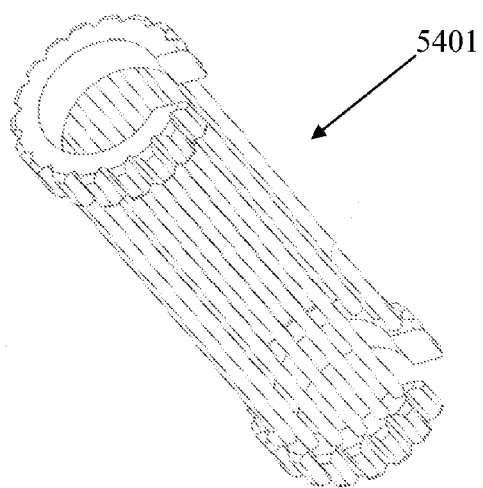
FIG. 54 illustrates an expandable device.

In similar construction an expandable device 5401 as shown in FIG. 54 is envisioned whereby the interdigitating interface to bone lies proximal and distal to the plurality of bars, rods, or other members that tie together both ends.

Figures 55, 56:
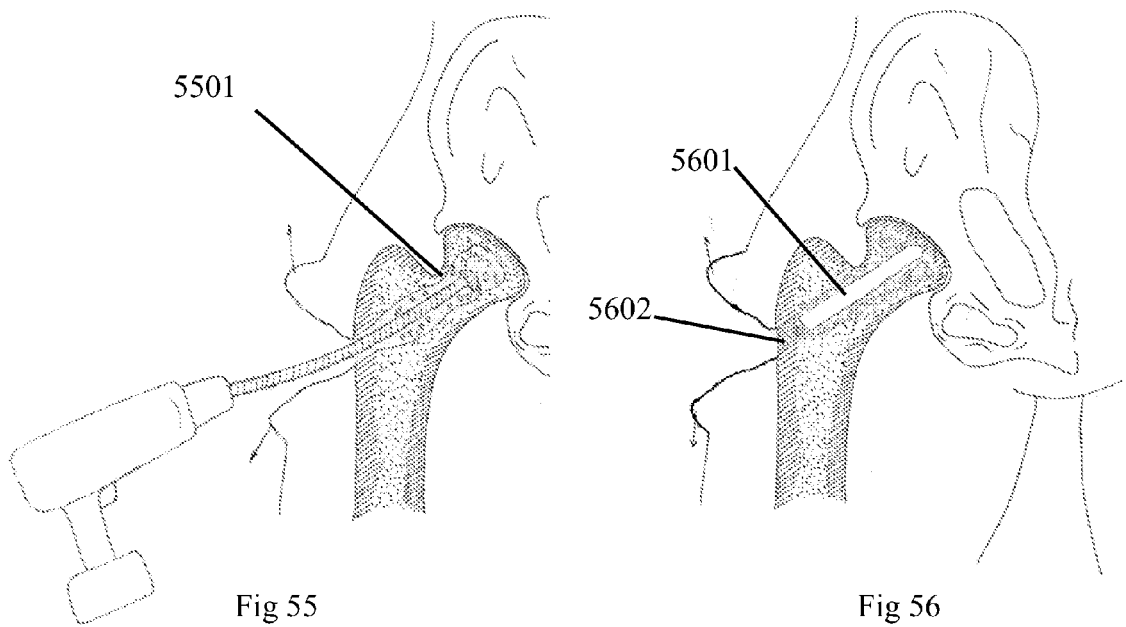
FIG. 55 illustrates a device coring into the upper trochanter region of the bone.
FIG. 56 illustrates delivery of a device into the upper trochanter.

In another example, the upper trochanteric region of the bone or other region of the musculo-skeletal system may be exposed and a hole may be cored out of the femoral neck 5501 as shown in FIG. 55. The reinforcement device (e.g., made of nitinol) is then delivered to the bore and expanded to fill the outside diameter of the hole 5601 as shown in FIG. 56. The inner diameter of the reinforcement device may be filled and pressurized with the bone cement. Alternatively, the inner diameter of the reinforcement device may be filled with the excised bone, bone plug or allographic bone 5602.

A corollary embodiment of the previously described art include axial translation from distal to proximal ends of the device thereby drawing bone and tissue together through shortening the axial distance distal to proximal. These embodiments have specific applications in fracture nonunions, joint fusions and certain fractures.

The devices disclosed herein can be deployed in a variety of suitable ways, as would be appreciated by those skilled in the art. For example, a provisional closed reduction of the fracture can be performed wherein a 1.5 to 2 inch incision is made overlying the metaphyseal prominence of the bone. Blunt dissection is then carried to the fascia whereupon the fascia is incised. The surgical approach to the central aspect (anterior-posterior) proceeds by either splitting the tendon or ligament or muscle longitudinally or by elevating structures of the bone in a subperiosteal fashion. The choice of the particular approach varies with respect to the fractured bone that is being treated. A specialized soft tissue retractor is placed onto the bone retracting the soft tissues away from the entry point of the bone.

A guide wire can then be drilled at an angle into the insertion point along the metaphyseal prominence. The angle of placement of the guide wire along the longitudinal axis of the bone depends on the fracture anatomy and particular bone being treated. The guide wire can then be placed under fluoroscopic guidance. An optimally chosen reamer is introduced over the guide wire opening the metaphyseal entry point. Both devices are then removed.

A curved guide wire is introduced across the open channel of the metaphysis and is advanced across the fracture site into the diaphysis of the bone. Sequential reaming appropriate for the particular device is performed to prepare the diaphysis. The distance from the fracture site to the entry point is estimated under fluoroscopy and the appropriate device is selected. The reamer is withdrawn and the device is introduced across the guide wire into the metaphysis and across the fracture into the diaphysis. Fluoroscopy confirms the location of the universal joint at the metaphyseal/diaphyseal fracture site.

The diaphyseal teeth of the device are deployed and the device is rigidly fixed to the diaphysis of the fractured bone distal to the fracture site. Any extension of the fracture into the joint can now be reduced in a closed fashion and held with K wires or in an open fashion via a dorsal approach to the intra-articular portion of the fracture. Metaphyseal locking flanges with targeting outriggers attached are now advanced (in to the metaphyseal bone) across the metaphyseal shaft. Using the attached targeting outrigger, guidewires are now placed through the metaphyseal locking flanges. The guidewires are directed fluoroscopically to stabilize the intra-articular portion of the fracture and/or to stabilize the metaphyseal fracture securely. Holes are drilled over the guidewires with a cannulated drill bit. Then, self tapping screws are advanced over the guidewires to lock the bone to the shaft and metaphyseal locking flange. The device is now locked within the proximal and distal bone fragments (metaphyseal or diaphyseal) and distal (diaphyseal) bone. This provides for rigid fixation of the comminuted intra-articular fragments to each other, and the fixation between these screws interlocking in to the metaphyseal flange component provides rigid fixation of these intra-articular fragments in the metaphyseal region to the diaphyseal shaft as well. The extremity and fracture is now manipulated until a satisfactory reduction is achieved as visualized under fluoroscopy. Thereafter, the fracture is manipulated under fluoroscopic guidance in order to achieve anatomic alignment of the bone fragments. Once optimal intramedullary reduction is achieved, the universal joint is locked. The fracture is now fixed securely. The guide wire is removed and the wound is closed repairing the periosteum over the metaphyseal entry point and repairing the fascia and closing the skin. A splint maybe applied.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treatment of an elongate bone, an intermedullary space extending along an axis of the bone, the bone having a fracture, the method comprising;
    forming an access opening traversing the intermedullary space at a placement angle to the axis of the bone;
    inserting a first end of a bone fixation device into the access opening, the bone fixation device having a flexible sleeve extending between the first end and a second end along a sleeve axis;
    advancing the bone fixation device from the access opening into the intermedullary space by flexing the sleeve in a plane along the sleeve axis;
    rigidly affixing a section of the bone fixation device to the bone adjacent the access opening, wherein the section spans the placement angle and rigidly supports the sleeve within the intramedullary space;
    locking the bone fixation device within the intramedullary space by rotating an actuator of the bone fixation device, the actuator oriented along the access opening and coupled with the second end of the sleeve by the section so that the actuator rotates about an axis of the access opening disposed at the placement angle to the axis of the bone wherein an elongate structure extends from the actuator and around the placement angle, the elongate structure having sufficient flexibility to transfer movement from the actuator to the sleeve when the placement angle is at least within a range of at least 30 to 45 degrees,
    and wherein the locking of the bone fixation device imposes an axial load on bearing surfaces disposed along the sleeve so as to stiffens the bone fixation device;
    deploying a plurality of teeth, with the elongate element and in response to rotating of the actuator, from an un-deployed configuration to a deployed configuration, the teeth in the un-deployed configuration disposed within an outer surface of the sleeve, the teeth in the deployed configuration extending radially outwardly from the outer surface of the sleeve through apertures in the sleeve and securing the sleeve within the intermedullary space of the bone.

2. The method of claim 1, wherein the elongate structure rotates about the axis of the access opening adjacent the actuator and transmits rotation around the placement angle so as to rotate about the sleeve axis within the intermedullary space during deployment, the rotation of the elongate structure urging the plurality of teeth radially outwardly, and wherein the placement angle is within a range from 30 to 45 degrees.

3. The method of claim 2, further comprising advancing a guidewire through the access opening and into the intermedullary space so that a bend of the guidewire extends around the placement angle between the access opening and the intermedullary space, a guidewire lumen extending axially within the bone fixation device; and
    wherein the bone fixation device is advanced axially while the guidewire is disposed within the guidewire lumen so that the guidewire axially guides the sleeve of the bone fixation device from the access opening, around the placement angle, and into the intermedullary space.

4. The method of claim 1, wherein the sleeve flexes sufficiently so that the lockable bone fixation device conforms anatomically to the bone, wherein flexing of the sleeve is accommodated by the bearing surfaces disposed along the length of the sleeve, and wherein rotation of the actuator imposes the axial load on the bearing surfaces so as to stiffen the lockable fixation device when the teeth are in the deployed configuration such that fixation of the fracture is effected.

5. The method of claim 1 wherein each tooth comprises a flexible structure and deploying the teeth bends the teeth radially from the un-deployed configuration to the deployed configuration, the bending of the teeth induced by threaded coupling of the actuator near the second end of the sleeve such that axial motion of the elongate structure is transmitted along the flexible sleeve to the teeth disposed at the first end.

6. The method of claim 1, further comprising removing the bone fixation device from the intermedullary space by articulation of the actuator so as to withdraw the teeth into the sleeve.

7. The method of claim 1, wherein the bone comprises a radius bone, and wherein the access aperture is formed through a laterally oriented bony protuberance of the radius bone so as to access the intermedullary space within the radius bone.

8. The method of claim 1, wherein each tooth is included in an associated anchoring segment, the anchoring segments comprising annular bodies from which the teeth extend, the annular bodies of the anchoring segments being separated axially and disposed within the sleeve, the sleeve having a cut extending circumferentially therethrough so as to flex axially between the annular bodies when the bone fixation device is inserted from the access opening into the intermedullary space, the annular bodies being urged axially by rotating of the actuator when deploying the teeth.

9. The method of claim 1 wherein the sleeve comprises a spiral cut through the sleeve and the sleeve flexes laterally in all directions when the device is advanced at the placement angle.

10. The method of claim 1 wherein the section comprises a universal joint with the elongate extending therethrough, and further comprising flexing of the universal joint to correspond to the placement angle during insertion of the sleeve, and locking the universal joint so that the section rigidly supports the sleeve within the intramedullary space.

* * * * *

UNITED STATES PATENT AND TRADEMARK OFFICE
CERTIFICATE OF CORRECTION

| PATENT NO. | : 7,914,533 B2 |
|---|---|
| APPLICATION NO. | : 11/565534 |
| DATED | : March 29, 2011 |
| INVENTOR(S) | : Charles L. Nelson, Heber Saravia and Kai U. Mazur |

It is certified that error appears in the above-identified patent and that said Letters Patent is hereby corrected as shown below:

| Issued Patent | | Description of Discrepancy |
|---|---|---|
| Column | Line | |
| Sheet 13 of 23 (Fig. 30A-30B) | 2 (Approx.) | Below "3000" insert --3010--. |
| 1 | 60 | Change "and or" to --and/or--. |
| 2 | 17 | Change "Raftopolous" to --Raftopoulos--. |
| 3 | 60 | Change "obdurator" to --obturator--. |
| 4 | 32 | Change "obdurator" to --obturator--. |
| 4 | 50-51 | Change "obdurator" to --obturator--. |
| 5 | 34 | Change "obdurator" to --obturator--. |
| 6 | 42 | Change "FIG. 4A-F" to --FIGS. 4A-F--. |
| 6 | 64 | Change "FIG.13 A-B" to --FIGS. 13A-B--. |
| 7 | 16 | Change "obdurator" to --obturator--. |
| 7 | 20 | Change "obdurator" to --obturator--. |
| 7 | 33 | Change "An" to --an--. |
| 9 | 61 | Change "obdurator" to --obturator--. |

Signed and Sealed this
Twentieth Day of September, 2011

David J. Kappos
*Director of the United States Patent and Trademark Office*

CERTIFICATE OF CORRECTION (continued)
U.S. Pat. No. 7,914,533 B2

| Col. | Line | Correction |
|---|---|---|
| 10 | 18 | Change "FIG. 4A-F," to --FIGS. 4A-F,--. |
| 10 | 37 | Change "FIG. 4D-E," to --FIGS. 4D-E,--. |
| 10 | 58-67 | Delete "513 or adapted to provide an indicator to facilitate deploying the teeth by providing an indication to the user of the relative position of the teeth relative to the slots on the sheath and relative to the plane within the bone. Thereby establishing the direction of flexibility of the device while in bone. Additionally, a central aperture 519 which forms a keyway can be provided for engaging an additional tool or device to control the deployment of the bone fixation device. For example, the central aperture 519 can be in the shape of a slit to accept, for example, the head of a flat head screw driver." and insert the same after "markings" on Col. 10, Line 57, as a continuation of same paragraph. |
| 11 | 62 | Change "950" to --950.--. |
| 12 | 35 | Change "obdurator" to --obturator--. |
| 12 | 53 | Change "obdurator" to --obturator--. |
| 13 | 59 | Change "obdurator" to --obturator--. |
| 13 | 62 | Change "obdurator" to --obturator--. |
| 13 | 63 | Change "obdurator" to --obturator--. |
| 14 | 1 | Change "obdurator" to --obturator--. |
| 14 | 45-46 | Change "deployment removal" to --deployment/removal--. |
| 15 | 31 | Change "drive" to --driver--. |
| 16 | 22 | Change "malleoulus" to --malleolus--. |
| 17 | 14 | Change "obdurator" to --obturator--. |
| 17 | 42-43 | Change "gentomiacin." to --gentamicin.--. |

CERTIFICATE OF CORRECTION (continued)
U.S. Pat. No. 7,914,533 B2

| | | |
|---|---|---|
| 17 | 59 | Change "itself" to --itself.--. |
| 18 | 28 | Change "polyphenylsolfone" to --polyphenylsulfone--. |
| 22 | 31 | In Claim 1, change "bone" to --bone,--. |
| 22 | 39 | In Claim 1, change "stiffens" to --stiffen--. |